(12) United States Patent
Albertsen et al.

(10) Patent No.: US 12,168,775 B2
(45) Date of Patent: Dec. 17, 2024

(54) COMPOSITIONS AND METHODS COMPRISING MALE FERTILITY SEQUENCES

(71) Applicant: PIONEER HI-BRED INTERNATIONAL, INC., Johnston, IA (US)

(72) Inventors: Marc C Albertsen, Grimes, IA (US); Andrew Mark Cigan, Madison, WI (US); Howard P Hershey, West Chester, PA (US); Michael Lassner, Portland, OR (US); Yongzhong Wu, Johnston, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 0 days.

(21) Appl. No.: 17/805,226

(22) Filed: Jun. 2, 2022

(65) Prior Publication Data

US 2022/0403411 A1    Dec. 22, 2022

Related U.S. Application Data

(63) Continuation of application No. 16/189,499, filed on Nov. 13, 2018, now Pat. No. 11,377,668, which is a continuation of application No. 14/425,916, filed as application No. PCT/US2013/058500 on Sep. 6, 2013, now Pat. No. 10,155,962.

(60) Provisional application No. 61/697,590, filed on Sep. 6, 2012.

(51) Int. Cl.
| | | |
|---|---|---|
| *A01H 5/10* | (2018.01) | |
| *A01H 1/00* | (2006.01) | |
| *A01H 6/46* | (2018.01) | |
| *C07K 14/415* | (2006.01) | |
| *C12N 15/82* | (2006.01) | |

(52) U.S. Cl.
CPC .......... *C12N 15/8289* (2013.01); *A01H 5/10* (2013.01); *A01H 6/4678* (2018.05); *C07K 14/415* (2013.01); *C12N 15/8287* (2013.01)

(58) Field of Classification Search
None
See application file for complete search history.

(56) References Cited

U.S. PATENT DOCUMENTS

| | | |
|---|---|---|
| 10,155,962 B2 | 12/2018 | Albertsen et al. |
| 11,377,668 B2 | 7/2022 | Albertsen et al. |
| 2006/0015968 A1 | 1/2006 | Albertsen et al. |
| 2006/0168696 A1 | 7/2006 | Feldmann et al. |
| 2006/0288440 A1 | 12/2006 | Albertsen et al. |
| 2007/0044171 A1 | 2/2007 | Kovalic et al. |
| 2007/0214517 A1 | 9/2007 | Alexandrov et al. |
| 2011/0173725 A1 | 7/2011 | Wu et al. |
| 2012/0005792 A1 | 1/2012 | Albertsen et al. |
| 2014/0075597 A1 | 3/2014 | Albertsen et al. |
| 2015/0252382 A1 | 9/2015 | Albertsen et al. |

FOREIGN PATENT DOCUMENTS

| | | |
|---|---|---|
| WO | 0206499 A2 | 1/2002 |
| WO | 20090250458 A1 | 2/2009 |
| WO | 2011/135527 | 4/2011 |
| WO | WO-2011060920 A2 | 5/2011 |
| WO | 2013/066423 A2 | 5/2013 |

OTHER PUBLICATIONS

GenBank Accession AK377076 dated May 20, 2011.
Gerola et al.: Sex, Plant Reprod., 2000, 12:347-352.
Hong, "Somatic and reproductive cell development in rice anther is regulated by a putative glurtaradoxin", The Plant Cell, (2012) 24:577-588.
Hedgcoth, "A chimeric open reading frame associated with cytoplasmic male sterility in alloplasmic wheat with Triticum timopheevi mitochondria is present in several *Triticum* and *Aegilops* species, barley and rye", Curr Genet (2002) 41:357-365.
Matsumoto et al., "Comprehensive Sequence Analysis of 24,783 Barley Full-Length cDNAs Derived from 12 Clone Libraries," Plant Physiology, (2011) 156:20-28.
Nelson et al., "P450 superfamily: update on new sequences, gene mapping, accession numbers and nomenclature," Pharmacogenetics, (1996) 61:21.
Unger, "Selection and orientation of adjacent genes influences DAM-mediated male sterility in transformed maize", (2001) 10:409-422.
UniProt Database Accession No. Q4KYG9; dated Aug. 2, 2005.
UniProt Database Accession No. F2ELP8; dated May 31, 2011.
Singh, Manjit; et al.: "MS26/CYP704B is required for anther and pollen wall development in bread wheat (*Triticum aestivum* L.) and combining mutations in all three homeologs causes male sterility," PLoS One 12(5): e0177632. May 16, 2017. pp. 1-16.
International Search Report and Written Opinion of the International Searching Authority for Application No. PCT/US2013/058500 dated Apr. 30, 2014.
International Preliminary Report on Patentability for International Application No. PCT/US2013/058500, mailed Mar. 19, 2015, 13 Pages.

*Primary Examiner* — Phuong T Bui

(57) ABSTRACT

Compositions and methods for modulating male fertility in a plant are provided. Compositions comprise nucleotide sequences, and active fragments and variants thereof, which modulate male fertility. Further provided are expression cassettes comprising the male fertility polynucleotides, or active fragments or variants thereof, operably linked to a promoter, wherein expression of the polynucleotides modulates the male fertility of a plant. Various methods are provided wherein the level and/or activity of the sequences that influence male fertility is modulated in a plant or plant part.

7 Claims, 4 Drawing Sheets
Specification includes a Sequence Listing.

FIG. 1

```
                          1                                                                      50
MS26TS         SEQ_21     ..............  ..............  ..............  ..............  ..............
Wheat A genome SEQ_28     GGAGGACGAC      GTGCTCCCGG      ACGGCACCAA      GGTGCGCGCC      ......GATGG
Wheat B genome SEQ_29     GGAGGACGAC      GTGCTCCCGG      ACGGCACCAA      GGTGCGCGCC      GGCGGGATGG
Wheat D genome SEQ_30     GGAGGACGAC      GTGCTCCCGG      ACGGCACCAA      GGTGCGCGCC      GGCGGGATGG
Maize MS26     SEQ_31     GGAGGACGAC      GTGCTGCCGG      ACGGGACGAA      GGTGAGGGCC      GGCGGGATGG
Sorghum MS26   SEQ_32     GGAGGACGAC      GTGCTGCCGG      ACGGGACGAA      GGTGAGGGCC      GGCGGGATGG
Rice MS26      SEQ_33     GGAGGACGAC      GTGCTCCCCG      ACGGCACCAA      GGTGCGCGCC      GGCGGGATGG 51
MS26TS         SEQ_21     TGACGTACGT      GCCCTAC...      ..............  ..............
Wheat A genome SEQ_28     TGACGTACGT      GCCCTACTCC      ATGGGGCGGA      TGGAG
Wheat B genome SEQ_29     TGACGTACGT      GCCCTACTCC      ATGGGGCGGA      TGGAG
Wheat D genome SEQ_30     TGACGTACGT      GCCCTACTCC      ATGGGGCGGA      TGGAG
Maize MS26     SEQ_31     TGACGTACGT      GCCCTACTCG      ATGGGGCGGA      TGGAG
Sorghum MS26   SEQ_32     TGACGTACGT      GCCCTACTCG      ATGGGGCGGA      TGGAG
Rice MS26      SEQ_33     TGACGTACGT      GCCCTACTCC      ATGGGGAGGA      TGGAG
```

FIG. 2

| SEQ ID NO: | Sequence |
|---|---|
| 34 | CGCGGGAGGACGACGTGCTCCCGGACGGCACCAAGGTGCGCGCCCGGGGATGGTGACGTACGTGCCCTACTCCATGGGGCGGATGGAGTACAACTGGGGC |
| 35 | AACCCGCGGGAGGACGACGTGCTCCCGGACGGCACCAAG----------------------------------------GTGCCCTACTCCATGGGGCGGATGGAGTACAACTGGGGC |
| 36 | AACCCGCGGGAGGACGACGTGCTCCCGGACGGCACCAAGGTGCGCGCCCGGCGATGGTGACGTAC--------TCCATGGGGCGGATGGAGTACAACTGGGGC |
| 37 | AACCCGCGGGAGGACGACGTGCTCCCGGACGGCACCAAGGTGCGCGCCCGGCG-------------------------GGATGGAGTACAACTGGGGC |
| 38 | AACCCGCGGGAGGACGACGTGCTCCCGGACGGCACCAAGGTGCGCGCCCGGCGATGGTGAC----GTGCCCTACTCCATGGGGCGGATGGAGTACAACTGGGGC |
| 39 | AACCCGCGGGAGGACGACGTGCTCCCGGACGGCACCAA----------------------------CGTGCCCTACTCCATGGGGCGGATGGAGTACAACTGGGGC |
| 40 | AACCCGCGGGAGGACGACGTGCTCCCGGACGGCACCAAGGTGCGCGCCCGGCGATGGTGACGTAC--------CCATGGGGCGGATGGAGTACAACTGGGGC |
| 41 | AACCCGCGGGAGGACGACGTGCTCCCGGACGGCACCAAGGTGCGCGCCCGGGAT-----------------ACTCCATGGGGCGGATGGAGTACAACTGGGGC |
| 42 | AACCCGCGGGAGGACGACGTGCTCCCGGACGGCACCAAG--------------------GTACGTGCCCTACTCCATGGGGCGGATGGAGTACAACTGGGGC |
| 43 | AACCCGCGGGAGGACGACGTGCTCCCGGACGGCACCAAGGTGCGCGCCCGGCGATGGTGACGTAC----TACTCCATGGGGCGGATGGAGTACAACTGGGGC |
| 44 | AACCCGCGGGAGGACGACGTGCTCCCGGACGGCACCAAGGTGCGCGCCCGGCGATG----------------TCCATGGGGCGGATGGAGTA |

FIG. 3

| PLANT NUMBER | MUTATION | MS26 ALLELE |
|---|---|---|
| 75 | 90 bp DEL | 1 |
| 64 | 96 bp DEL | 1 |
| 120 | 23 bp DEL | 1 |
| 14 | GTAC DEL | 2 |
| 45 | C insert | 2 |
| 9 | 81 bp DEL | 3 |
| 30 | 9 bp DEL | 3 |

FIG. 4

```
SEQ ID
NO:
21                                                                                                     GATGTGACGTAC GTGCCCTAC
45  CTCCGCCCTGTACCCGGCCGTCCCCAGGACCCCAAGGGCATCGCGGAGGACGACGTGCTCCCCGACGGCGACCACCAAGGTGCCGCCCGGCGGCCGGATGAGTGACGTAC GTGCCCTACTCCATGGGCCGGATGGAGTACAACTGGGCCCGACGCCGGCCAGC
46  CTCCGCCTGTAC------------------------------------------------------------------------------------------------GTGCCCTACTCCATGGGCCGGATGGAGTACAACTGGGCCCCGACGCCGGCCAGC
47  CTCCGCCTGTACCCGGCCGTCCCCAGGACCCCAAGGGCATCGCGGAGGACGACGT--------------------------------------------------------------------------------------------------CGGC
48  CTCCGCCTGTACCCGGCCGTCCCCAGGACCCCAAGGGCATCGCGGAGGACGACGTGCTCCCGGACGGCGACCACCAAGGTACTGCC------CTACTCCATGGGCCGGATGGAGTACAACTGGGCCCCGACGCCGGCCAGC
49  CTCCGCCTGTACCCGGCCGTCCCCAGGACCCCAAGGGCATCGCGGAGGACGACGTGCTCCCGGACGGCGACCACCAAGGTGCCGCCCCCGGCGGATGGTGACGT------GCCCTACTCCATGGGCCGGATGGAGTACAACTGGGCCCCGACGCCGCCAGC
50  CTCCGCCTGTACCCGGCCGTCCCCAGGACCCCAAGGGCATCGCGGAGGACGACGTGCTCCCCGACGGCGACCACCAAGGTGCCGCCCCGGCGGATGGTGACGTACGTGCCCTACTCCGTCCCCTACTCCATGGGCCGGATGGAGTACAACTGGGCCCCGACGCCGCCAGC
51  CTCCGCCTGTACCCGGCCGTCCCCAGGACCCCAAGGGCATCGCGGAGGACGACGTGCTC--------------------------------------------------------------------------CCGGACGGCACCAAG
52  CTCCGCCTGTACCCGGCCGTCCCCAGGACCCCAAGGGCATCGCGGAGGACGACGTGCTCCCGGACGGCGACCACCAAGGTGCCGCCCCGGCGGATGGTGACGTAC----------TCCATGGGCCGGATGGAGTACAACTGGGCCCCGACGCCGCCAGC
```

COMPOSITIONS AND METHODS COMPRISING MALE FERTILITY SEQUENCES

CROSS-REFERENCE TO RELATED APPLICATIONS

This application is a continuation of U.S. patent application Ser. No. 16/189,499, filed Nov. 13, 2018, now U.S. Pat. No. 11,377,668, issued Jul. 5, 2022, which is a continuation of U.S. patent application Ser. No. 14/425,916, filed Mar. 4, 2015, now U.S. Pat. No. 10,155,962, issued Dec. 18, 2018, which is a 371 national stage entry of PCT patent application PCT/US13/058500, filed Sep. 6, 2013, which claims benefit of and priority to Provisional Application No. 61/697,590, filed Sep. 6, 2012, each of which is incorporated herein by reference in its entirety.

FIELD OF THE INVENTION

The present invention relates to the field of plant molecular biology, more particularly to influencing male fertility.

REFERENCE TO ELECTRONICALLY-SUBMITTED SEQUENCE LISTING

The official copy of the sequence listing is submitted electronically via EFS-Web as an ASCII formatted sequence listing with a file named 5282-PCT_ST25.txt, last modified on Sep. 6, 2013, having a size of 42 KB, and is filed concurrently with the specification. The sequence listing contained in this ASCII formatted document is part of the specification and is herein incorporated by reference in its entirety.

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant.

In certain species, such as *Brassica campestris*, the plant is normally self-sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Bread wheat (*Triticum aestivum*) is a hexaploid plant having three pairs of homologous chromosomes defining genomes A, B and D. The endosperm of wheat grain comprises 2 haploid complements from a maternal cell and 1 from a paternal cell. The embryo of wheat grain comprises one haploid complement from each of the maternal and paternal cells. Hexaploidy has been considered a significant obstacle in researching and developing useful variants of wheat. In fact, very little is known regarding how homologous genes of wheat interact, how their expression is regulated, and how the different proteins produced by homologous genes function separately or in concert.

An essential aspect of much of the work underway with genetic male sterility systems is the identification of genes influencing male fertility. Such a gene can be used in a variety of systems to control male fertility including those described herein.

BRIEF SUMMARY OF THE INVENTION

Compositions and methods for modulating male fertility in a plant are provided. Compositions comprise nucleotide sequences, and active fragments and variants thereof, which modulate male fertility. Further provided are expression cassettes comprising one or more of the male fertility polynucleotides, or active fragments or variants thereof, operably linked to a promoter, wherein expression of the polynucleotides modulates the male fertility of a plant. Various methods are provided wherein the level and/or activity of a polynucleotide that influences male fertility is modulated in a plant or plant part.

DESCRIPTION OF THE FIGURES

FIG. 1 shows an alignment of the Wheat MS26 genes, A (SEQ ID NO: 28), B (SEQ ID NO: 29) and D (SEQ ID NO: 30) genomes, across the MS26+ target site (SEQ ID NO: 21) compared to the maize (SEQ ID NO: 31), sorghum (SEQ ID NO: 32) and rice (SEQ ID NO: 33) MS26 orthologous genes.

FIG. 2 shows an alignment of the NHEJ mutations induced by the MS26+ homing endonuclease, described herein. The mutations were identified by deep sequencing. The reference illustrates the unmodified locus with the genomic target site underlined. The expected site of cleavage is also indicated. Deletions as a result of imperfect NHEJ are shown by a "-". The reference corresponds to Fielder wheat Ms26 (SEQ ID NO: 34).

FIG. 3 shows types of NHEJ mutations induced by the MS26+ homing endonuclease, described herein. The mutations were identified by sequencing of subcloned PCR products in DNA vectors. MS26 allele designation 1, 2, and 3 likely refers to wheat genome copy D, A and B respectively.

FIG. 4 shows an alignment of the NHEJ mutations induced by the MS26+ homing endonuclease. The top sequence is the MS26 target site (SEQ ID NO: 21) compared to a reference sequence (SEQ ID NO: 45) which illustrates the unmodified locus. Deletions as a result of imperfect NHEJ are shown by a "-", while the gap represents a C nucleotide insertion in SEQ ID NO: 50. The mutations were identified by sequencing of subcloned PCR products in DNA vectors.

DETAILED DESCRIPTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Male Fertility Polynucleotides

Compositions disclosed herein include polynucleotides and polypeptides that influence male fertility. In particular, isolated polynucleotides are provided comprising nucleotide sequences encoding the amino acid sequences set forth in SEQ ID NOS: 2, 4, 6, 8, 10, 12, 14, 16, or 18 or active fragments or variants thereof. Further provided are polypeptides having an amino acid sequence encoded by a polynucleotide described herein, for example those set forth in SEQ ID NOS:1, 3, 5, 7, 9, 11, 13, 15, or 17 or active fragments or variants thereof.

Sexually reproducing plants develop specialized tissues specific for the production of male and female gametes. Successful production of male gametes relies on proper formation of the male reproductive tissues. The stamen, which embodies the male reproductive organ of plants, contains various cell types, including for example, the filament, anther, tapetum, and pollen. As used herein, "male tissue" refers to the specialized tissue in a sexually reproducing plant that is responsible for production of the male gamete. Male tissues include, but are not limited to, the stamen, filament, anther, tapetum, and pollen.

The process of mature pollen grain formation begins with microsporogenesis, wherein meiocytes are formed in the sporogenous tissue of the anther. Microgametogenesis follows, wherein microspores divide mitotically and develop into the microgametophyte, or pollen grains. The condition of "male fertility" or "male fertile" refers to those plants producing a mature pollen grain capable of fertilizing a female gamete to produce a subsequent generation of offspring. The term "influences male fertility" or "modulates male fertility", as used herein, refers to any increase or decrease in the ability of a plant to produce a mature pollen grain when compared to an appropriate control. A "mature pollen grain" or "mature pollen" refers to any pollen grain capable of fertilizing a female gamete to produce a subsequent generation of offspring. Likewise, the term "male fertility polynucleotide" or "male fertility polypeptide" refers to a polynucleotide or polypeptide that modulates male fertility. A male fertility polynucleotide may, for example, encode a polypeptide that participates in the process of microsporogenesis or microgametogenesis.

Male fertility polynucleotides disclosed herein include homologs and orthologs of polynucleotides shown to influence male fertility. For example, male fertility polynucleotides, and active fragments and variants thereof, disclosed herein include homologs and orthologs of Ms22 (also referred to as Mscal). Mutagenesis studies of Ms22 resulted in phenotypically male sterile maize plants with anthers that did not extrude from the tassel and lacked sporogenous tissue. West and Albertsen (1985) *Maize Newsletter* 59:87; Neuffer et al. (1977) Mutants of maize. Cold Spring Harbor Laboratory Press, Cold Spring Harbor, NY.

Plants deficient in Ms22 expression exhibit physiological changes early in reproductive-tissue development. Ms22 is believed to have a role in another development that occurs earlier than that of Ms45 or Ms26. Certain male sterility genes such as MAC1, EMS1 or GNE2 (Sorensen et al. (2002) *Plant J.* 29:581-594) prevent cell growth in the quartet stage. Mutations in the SPOROCYTELESS/ NOZZLE gene act early in development, but impact both anther and ovule formation such that plants are male and female sterile. The SPOROCYTELESS gene of *Arabidopsis* is required for initiation of sporogenesis and encodes a novel nuclear protein (*Genes Dev.* 1999 Aug. 15; 13(16):2108-17). Because Ms22 is critical for the progression of microsporogenesis, maintenance of male sterility in Ms22 mutants is very reliable compared to other male sterility mutant constructs. As disclosed elsewhere herein, Ms22 polynucleotides from wheat are set forth in SEQ ID NOs: 1, 3, and 5.

Additional male fertility polynucleotides include the Ms26 polynucleotide and homologs and orthologs thereof. Ms26 polypeptides have been reported to have significant homology to P450 enzymes found in yeast, plants, and mammals. P450 enzymes have been widely studied and characteristic protein domains have been elucidated. The Ms26 protein contains several structural motifs characteristic of eukaryotic P450's, including the heme-binding domain FxxGxRxCxG (domain D; SEQ ID NO: 19), domain AA/GGXD/ETT/S (dioxygen-binding; SEQ ID NO: 20), domain B (steroid-binding) and domain C. Phylogenetic tree analysis revealed that Ms26 is most closely related to P450s involved in fatty acid omega-hydroxylation found in *Arabidopsis thaliana* and *Vicia sativa*. See, for example, US Patent Publication No. 2012/0005792, herein incorporated by reference. As disclosed elsewhere herein, Ms26 polynucleotides from wheat are set forth in SEQ ID NOs: 7, 9, and 11.

Additional male fertility polynucleotides, and active fragments and variants thereof, disclosed herein may also include homologs and orthologs of Ms45 polynucleotides. The Ms45 polynucleotide is a male fertility polynucleotide characterized in maize. Mutations of Ms45 can result in breakdown of microsporogenesis during vacuolation of the microspores rendering the mutated plants male sterile. When the cloned maize Ms45 polynucleotide is introduced into such mutated male sterile plants, the gene can complement the mutation and confer male fertility. As disclosed elsewhere herein, Ms45 polynucleotides from wheat are set forth in SEQ ID NOs: 13, 15, and 17.

Strategies for manipulation of expression of male-fertility polynucleotides in wheat will require consideration of the ploidy level of the individual wheat variety. *Triticum aestivum* is a hexaploid containing three genomes designated A, B, and D (N=21); each genome comprises seven pairs of nonhomologous chromosomes. Einkorn wheat varieties are diploids (N=7) and emmer wheat varieties are tetraploids (N=14).

Isolated or substantially purified nucleic acid molecules or protein compositions are disclosed herein. An "isolated" or "purified" nucleic acid molecule, polynucleotide, or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the polypeptides disclosed herein or biologically active portion thereof is recombinantly produced, optimally culture medium represents less than about 30%, 20%, 10%, 5%, or 1% (by dry weight) of chemical precursors or non-protein-of-interest chemicals.

A "subject plant" or "subject plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or plant cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

A. Fragments and Variants of Male Fertility Sequences

Fragments and variants of the disclosed polynucleotides and proteins encoded thereby are also provided. By "fragment" is intended a portion of the polynucleotide or a portion of the amino acid sequence and hence protein encoded thereby. Fragments of a polynucleotide may encode protein fragments that retain the biological activity of the native protein and hence influence male fertility. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide encoding the polypeptides disclosed herein.

A fragment of a polynucleotide that encodes a biologically active portion of a polypeptide that influences male fertility will encode at least 15, 25, 30, 50, 100, 150, 200, 250, 300, 350, 400, 450, 500, 525, or 537 contiguous amino acids, or up to the total number of amino acids present in a full-length polypeptide that influences male fertility (for example, SEQ ID NO: 2, 4, 6, 8, 10, 12, 14, 16, and 18, respectively). Fragments of a polynucleotide encoding a polypeptide that influences male fertility that are useful as hybridization probes or PCR primers generally need not encode a biologically active portion of a polypeptide that influences male fertility.

Thus, a fragment of a male fertility polynucleotide as disclosed herein may encode a biologically active portion of a male fertility polypeptide, or it may be a fragment that can be used as a hybridization probe or PCR primer using methods disclosed below. A biologically active portion of a male fertility polypeptide can be prepared by isolating a portion of one of the male fertility polynucleotides disclosed herein, expressing the encoded portion of the male fertility protein (e.g., by recombinant expression in vitro), and assessing the activity of the encoded portion of the male fertility polypeptide. Polynucleotides that are fragments of a male fertility polynucleotide comprise at least 16, 20, 50, 75, 100, 150, 200, 250, 300, 350, 400, 450, 500, 550, 600, 650, 700, 800, 900, 1000, 1100, 1200, 1300, 1400, 1500, 1600, or 1629 nucleotides, or up to the number of nucleotides present in a full-length male fertility polynucleotide disclosed herein (i.e., SEQ ID NOS:1, 3, 5, 7, 9, 11, 13, 15, or 17, respectively).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the male fertility polypeptides disclosed herein. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a male fertility polypeptide. Generally, variants of a particular polynucleotides disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide (e.g., any one of SEQ ID NOS:1, 3, 5, 7, 9, 11, 13, 15, or 17) as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2, 4, 6, 8, 10, 12, 14, 16, or 18 are disclosed. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins disclosed herein are biologically active, that is they continue to possess the desired biological activity of the native protein, that is, male fertility activity as described herein. Such variants may result from, for example, genetic polymorphism or from human manipulation. Biologically active variants of a male fertility protein disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein (e.g. any one of SEQ ID NO: 2, 4, 6, 8, 10, 12, 14, 16, or 18) as determined by sequence alignment programs and parameters described elsewhere herein. A biologically active variant of a protein disclosed herein may differ from that protein by as few as 1-15 amino acid residues, as few as 1-10, such as 6-10, as few as 5, as few as 4, 3, 2, or even 1 amino acid residue.

The proteins disclosed herein may be altered in various ways including amino acid substitutions, deletions, truncations, and insertions. Methods for such manipulations are generally known in the art. For example, amino acid sequence variants and fragments of the male fertility polypeptides can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides disclosed herein include both the naturally occurring sequences as well as DNA sequence variants which retain function. Likewise, the male fertility polypeptides and proteins encompass both naturally occurring polypeptides as well as variations and modified forms thereof. Such polynucleotide and polypeptide variants will continue to possess the desired male fertility activity. The mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for male fertility activity.

Increases or decreases in male fertility can be assayed in a variety of ways. One of ordinary skill in the art can readily assess activity of the variant or fragment by introducing the polynucleotide into a plant homozygous for a stable male sterile allele of the polynucleotide, and observing male tissue development in the plant. For example, to assay for male fertility activity of Ms22 (i.e. SEQ ID NO: 1, 3, or 5), one of skill in the art can begin by constructing a plant homozygous for a mutation in the native Ms22 gene resulting in male sterility. Subsequently, one could complement the mutation by providing the Ms22 polynucleotide, or active fragment or variant thereof, and observing whether the male tissues of the plant develop normally and are able to produce mature pollen. Likewise, the same procedure can be carried out to assay for the male fertility activity of variants or fragments of Ms26 (i.e. SEQ ID NO: 7, 9, or 11) or Ms45 (i.e. SEQ ID NO: 13, 15, or 17), also disclosed herein.

Variant functional polynucleotides and proteins also encompass sequences and proteins derived from a mutagenic and recombinogenic procedure such as DNA shuffling. With such a procedure, one or more different male fertility sequences can be manipulated to create a new male fertility polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the male fertility polynucleotides disclosed herein and other known male fertility polynucleotides to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

II. Sequence Analysis

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The use of the term "polynucleotide" is not intended to limit the present disclosure to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides disclosed herein also encompass all forms of sequences including, but not limited to, single-stranded forms, double-stranded forms, hairpins, stem-and-loop structures, and the like.

III. Expression Cassettes

The male fertility polynucleotides disclosed herein can be provided in expression cassettes for expression in an organism of interest. The cassette can include 5' and 3' regulatory sequences operably linked to a male fertility polynucleotide as disclosed herein. "Operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

The expression cassettes disclosed herein may include in the 5'-3' direction of transcription, a transcriptional and translational initiation region (i.e., a promoter), a polynucleotide of interest, and a transcriptional and translational termination region (i.e., termination region) functional in the host cell (i.e., the plant). Expression cassettes are also provided with a plurality of restriction sites and/or recombination sites for insertion of the male fertility polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein. For example, the male fertility polynucleotides disclosed herein may be stacked with any other polynucleotides encoding male-gamete disruptive polynucleotides or polypeptides, cytotoxins, markers, or other male fertility sequences as disclosed elsewhere herein. The stacked polynucleotides may be operably linked to the same promoter as the male fertility polynucleotide, or may be operably linked to a separate promoter polynucleotide.

As described elsewhere herein, expression cassettes may comprise a promoter operably linked to a polynucleotide of interest, along with a corresponding termination region. The termination region may be native to the transcriptional initiation region, may be native to the operably linked male fertility polynucleotide of interest or with the male fertility promoter sequences, may be native to the plant host, or may be derived from another source (i.e., foreign or heterologous). Convenient termination regions are available from the Ti-plasmid of *A. tumefaciens*, such as the octopine synthase and nopaline synthase termination regions. See also Guerineau et al. (1991) *Mol Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A. Expression Cassettes Comprising a Male Fertility Polynucleotide

In particular embodiments, the expression cassettes disclosed herein comprise a promoter operably linked to a male fertility polynucleotide, or active fragment or variant thereof, as disclosed herein. In certain embodiments, a male fertility promoter or an active fragment or variant thereof, is operably linked to a male fertility polynucleotide disclosed herein, such as the male fertility polynucleotide set forth in SEQ ID NO: 1, 3, 5, 7, 9, 11, 13, 15, or 17, or an active fragment or variant thereof.

In certain embodiments, plant promoters can preferentially initiate transcription in certain tissues, such as stamen, anther, filament, and pollen, or developmental growth stages, such as sporogenous tissue, microspores, and microgametophyte. Such plant promoters are referred to as "tissue-preferred", "cell type-preferred", or "growth-stage preferred". Promoters which initiate transcription only in certain tissue are referred to as "tissue-specific". Likewise, promoters which initiate transcription only at certain growth stages are referred to as "growth stage-specific". A "cell type-specific" promoter drives expression only in certain cell types in one or more organs, for example, stamen cells, or individual cell types within the stamen such as anther, filament, or pollen cells.

Male fertility polynucleotides disclosed herein, and active fragments and variants thereof, can be operably linked to male-tissue-specific or male-tissue-preferred promoters including, for example, stamen-specific or stamen-preferred promoters, anther-specific or anther-preferred promoters, pollen-specific or pollen-preferred promoters, tapetum-specific promoters or tapetum-preferred promoters, and the like. Promoters can be selected based on the desired outcome. For example, the polynucleotides of interest can be operably linked to constitutive, tissue-preferred, growth stage-preferred, or other promoters for expression in plants.

In one embodiment, the promoters may be those which preferentially express a polynucleotide of interest in the male tissues of the plant. No particular male fertility tissue-preferred promoter must be used in the process, and any of the many such promoters known to one skilled in the art may be employed. One such promoter is the 5126 promoter, which preferentially directs expression of the polynucleotide to which it is linked to male tissue of the plants, as described in U.S. Pat. Nos. 5,837,851 and 5,689,051. Other examples include the maize Ms45 promoter described at U.S. Pat. No. 6,037,523; SF3 promoter described at U.S. Pat. No. 6,452, 069; the BS92-7 promoter described at WO 02/063021; a SGB6 regulatory element described at U.S. Pat. No. 5,470, 359; the TA29 promoter (Koltunow, et al., (1990) Plant Cell 2:1201-1224; Goldberg, et al., (1993) Plant Cell 5:1217-1229 and U.S. Pat. No. 6,399,856); the type 2 metallothionein-like gene promoter (Charbonnel-Campaa, et al., Gene (2000) 254:199-208) and the Brassica Bca9 promoter (Lee, et al., (2003) Plant Cell Rep. 22:268-273).

In some embodiments, expression cassettes comprise male-gamete-preferred promoters operably linked to a male fertility polynucleotide. Male-gamete-preferred promoters include the PG47 promoter (U.S. Pat. Nos. 5,412,085; 5,545,546; *Plant J* 3(2):261-271 (1993)), as well as ZM13 promoter (Hamilton, et al., (1998) Plant Mol. Biol. 38:663-669); actin depolymerizing factor promoters (such as Zmabp1, Zmabp2; see, for example Lopez, et al., (1996) Proc. Natl. Acad. Sci. USA 93:7415-7420); the promoter of the maize pectin methylesterase-like gene, ZmC5 (Wakeley, et al., (1998) Plant Mol. Biol. 37:187-192); the profilin gene promoter Zmpro1 (Kovar, et al., (2000) The Plant Cell 12:583-598); the sulphated pentapeptide phytosulphokine gene ZmPSK1 (Lorbiecke, et al., (2005) Journal of Experimental Botany 56(417):1805-1819); the promoter of the calmodulin binding protein Mpcbp (Reddy, et al., (2000) J. Biol. Chem. 275(45):35457-70).

As disclosed herein, constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

"Seed-preferred" promoters include both those promoters active during seed development such as promoters of seed storage proteins as well as those promoters active during seed germination. See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference. Additional embryo specific promoters are disclosed in Sato et al. (1996) *Proc. Natl. Acad. Sci.* 93:8117-8122; Nakase et al. (1997) *Plant J* 12:235-46; and Postma-Haarsma et al. (1999) *Plant Mol. Biol.* 39:257-71. Additional endosperm specific promoters are disclosed in Albani et al. (1984) *EMBO* 3:1405-15; Albani et al. (1999) *Theor. Appl. Gen.* 98:1253-62; Albani et al. (1993) *Plant J.* 4:343-55; Mena et al. (1998) *The Plant Journal* 116:53-62, and Wu et al. (1998) *Plant Cell Physiology* 39:885-889.

Dividing cell or meristematic tissue-preferred promoters have been disclosed in Ito et al. (1994) *Plant Mol. Biol.* 24:863-878; Reyad et al. (1995) *Mo. Gen. Genet.* 248:703-711; Shaul et al. (1996) *Proc. Natl. Acad. Sci.* 93:4868-4872; Ito et al. (1997) *Plant J.* 11:983-992; and Trehin et al. (1997) *Plant Mol. Biol.* 35:667-672.

Stress inducible promoters include salt/water stress-inducible promoters such as P5CS (Zang et al. (1997) *Plant Sciences* 129:81-89); cold-inducible promoters, such as, cor15a (Hajela et al. (1990) *Plant Physiol.* 93:1246-1252), cor15b (Wlihelm et al. (1993) *Plant Mol Biol* 23:1073-1077), wsc120 (Ouellet et al. (1998) *FEBS Lett.* 423-324-328), ci7 (Kirch et al. (1997) *Plant Mol Biol.* 33:897-909), ci21A (Schneider et al. (1997) *Plant Physiol.* 113:335-45); drought-inducible promoters, such as, Trg-31 (Chaudhary et al (1996) *Plant Mol. Biol.* 30:1247-57), rd29 (Kasuga et al. (1999) *Nature Biotechnology/*8:287-291); osmotic inducible promoters, such as, Rab 17 (Vilardell et al. (1991) *Plant Mol. Biol.* 17:985-93) and osmotin (Raghothama et al. (1993) *Plant Mol Biol* 23:1117-28); and, heat inducible promoters, such as, heat shock proteins (Barros et al. (1992) *Plant Mol.* 19:665-75; Marrs et al. (1993) *Dev. Genet.* 14:27-41), and smHSP (Waters et al. (1996) *J. Experimental Botany* 47:325-338). Other stress-inducible promoters include rip2 (U.S. Pat. No. 5,332,808 and U.S. Publication No. 2003/0217393) and rp29a (Yamaguchi-Shinozaki et al. (1993) *Mol. Gen. Genetics* 236:331-340).

As discussed elsewhere herein, the expression cassettes comprising male fertility polynucleotides may be stacked with other polynucleotides of interest. Any polynucleotide of interest may be stacked with the male fertility polynucleotide, including for example, male-gamete-disruptive polynucleotides and marker polynucleotides.

Male fertility polynucleotides disclosed herein may be stacked in or with expression cassettes comprising a promoter operably linked to a polynucleotide which is male-gamete-disruptive; that is, a polynucleotide which interferes with the function, formation, or dispersal of male gametes. A male-gamete-disruptive polynucleotide can operate to prevent function, formation, or dispersal of male gametes by any of a variety of methods. By way of example but not limitation, this can include use of polynucleotides which encode a gene product such as DAM-methylase or barnase (See, for example, U.S. Pat. No. 5,792,853 or 5,689,049; PCT/EP89/00495); encode a gene product which interferes with the accumulation of starch or affects osmotic balance in pollen (See, for example, U.S. Pat. Nos. 7,875,764; 8,013,218; 7,696,405); inhibit formation of a gene product important to male gamete function, formation, or dispersal (See, for example, U.S. Pat. Nos. 5,859,341; 6,297,426); encode a gene product which combines with another gene product to prevent male gamete formation or function (See U.S. Pat. Nos. 6,162,964; 6,013,859; 6,281,348; 6,399,856; 6,248,935; 6,750,868; 5,792,853); are antisense to, or cause co-suppression of, a gene critical to male gamete function, formation, or dispersal (See U.S. Pat. Nos. 6,184,439; 5,728,926; 6,191,343; 5,728,558; 5,741,684); interfere with expression of a male fertility polynucleotide through use of hairpin formations (Smith et al. (2000) Nature 407:319-320; WO 99/53050 and WO 98/53083) or the like.

Male-gamete-disruptive polynucleotides include dominant negative genes such as methylase genes and growth-inhibiting genes. See, U.S. Pat. No. 6,399,856. Dominant negative genes include diphtheria toxin A-chain gene (Czako and An (1991) Plant Physiol. 95 687-692; Greenfield et al. (1983) PNAS 80:6853; cell cycle division mutants such as CDC in maize (Colasanti et al. (1991) PNAS 88: 3377-3381); the WT gene (Farmer et al. (1994) Mol. Genet. 3:723-728); and P68 (Chen et al. (1991) PNAS 88:315-319).

Further examples of male-gamete-disruptive polynucleotides include, but are not limited to, pectate lyase gene pelE from *Erwinia chrysanthermi* (Kenn et al (1986) J. Bacteriol. 168:595); CytA toxin gene from *Bacillus thuringiensis* Israeliensis (McLean et al (1987) J. Bacteriol. 169:1017 (1987), U.S. Pat. No. 4,918,006); DNAses, RNAses, proteases, or polynucleotides expressing anti-sense RNA. A male-gamete-disruptive polynucleotide may encode a protein involved in inhibiting pollen-stigma interactions, pollen tube growth, fertilization, or a combination thereof.

Male fertility polynucleotides disclosed herein may be stacked with expression cassettes disclosed herein comprising a promoter operably linked to a polynucleotide of interest encoding a reporter or marker product. Examples of suitable reporter polynucleotides known in the art can be found in, for example, Jefferson et al. (1991) in Plant Molecular Biology Manual, ed. Gelvin et al. (Kluwer Academic Publishers), pp. 1-33; DeWet et al. Mol. Cell. Biol. 7:725-737 (1987); Goff et al. EMBO J. 9:2517-2522 (1990); Kain et al. BioTechniques 19:650-655 (1995); and Chiu et al. Current Biology 6:325-330 (1996). In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate, and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase, and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene, and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP), and DsRed2 where plant cells transformed with the marker gene are red in color, and thus visually selectable. Additional examples include a p-lactamase gene encoding an enzyme for which various chromogenic substrates are known (e.g., PADAC, a chromogenic cephalosporin), a xy1E gene encoding a catechol dioxygenase that can convert chromogenic catechols, an α-amylase gene, and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad Aci. USA* 86:5400-5404; Fuerst et al. (1989) *Proc. Natl. Acad Sci. USA* 86:2549-2553; Deuschle et al. (1990) *Science* 248:480-483; Gossen (1993) Ph.D. Thesis, University of Heidelberg; Reines et al. (1993) *Proc. Natl. Acad Sci. USA* 90:1917-1921; Labow et al. (1990) *Mol Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) Proc. *Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions and methods disclosed herein.

In some embodiments, the expression cassettes disclosed herein comprise a first polynucleotide of interest encoding a male fertility polynucleotide operably linked to a first promoter polynucleotide stacked with a second polynucleotide of interest encoding a male-gamete-disruptive gene product operably linked to a male tissue-preferred promoter polynucleotide. In other embodiments, the expression cassettes described herein may also be stacked with a third polynucleotide of interest encoding a marker polynucleotide operably linked to a third promoter polynucleotide.

In specific embodiments, the expression cassettes disclosed herein comprise a first polynucleotide of interest encoding a wheat male fertility gene disclosed herein, such as Ms22, Ms26, or Ms45 operably linked to a constitutive promoter, such as the cauliflower mosaic virus (CaMV) 35S promoter. The expression cassettes may further comprise a second polynucleotide of interest encoding a male-gamete-disruptive gene product operably linked to a male tissue-preferred promoter. In certain embodiments, the expression cassettes disclosed herein may further comprise a third polynucleotide of interest encoding a marker gene, such as the phosphinothricin acetyltransferase (PAT) gene from *Streptomyces viridochomagenes* operably linked to a constitutive promoter, such as the cauliflower mosaic virus (CaMV) 35S promoter.

IV. Plants

A. Plants Having Altered Levels/Activity of Male Fertility Polypeptide

Further provided are plants having altered levels and/or activities of a male fertility polypeptide and/or altered levels of male fertility. In some embodiments, the plants disclosed herein have stably incorporated into their genomes a heterologous male fertility polynucleotide, or active fragments or variants thereof, as disclosed herein. Thus, plants, plant cells, plant parts, and seeds are provided which comprise at least one heterologous male fertility polynucleotide as set forth in any one of SEQ ID NO: 1, 3, 5, 7, 9, 11, 13, 15, or 17 or any active fragments or variants disclosed herein.

Plants are further provided comprising the expression cassettes disclosed herein comprising a male fertility polynucleotide operably linked to a promoter that is active in the plant. In some embodiments, expression of the male fertility polynucleotide modulates male fertility of the plant. In certain embodiments, expression of the male fertility polynucleotide increases male fertility of the plant. For example, plants are provided comprising an expression cassette comprising an Ms22 polynucleotide as set forth in SEQ ID NO: 1, 3, or 5, or an active fragment or variant thereof, operably linked to a constitutive promoter, such as the CaMV 35S promoter. Upon expression of the Ms22 polynucleotide, male fertility of the plant is increased.

In certain embodiments, expression cassettes comprising a heterologous male fertility polynucleotide as disclosed herein, or an active fragment or variant thereof, operably linked to a promoter active in a plant, are provided to a male sterile plant. Upon expression of the heterologous male fertility polynucleotide, the male fertility of the plant is restored. In specific embodiments, the plants disclosed herein comprise an expression cassette comprising a heterologous male fertility polynucleotide as disclosed herein, or an active fragment or variant thereof, operably linked to a promoter, stacked with one or more expression cassettes comprising a polynucleotide of interest operably linked to a promoter active in the plant. For example, the stacked polynucleotide of interest can comprise a male-gamete-disruptive polynucleotide and/or a marker polynucleotide.

Plants disclosed herein may also comprise stacked expression cassettes described herein comprising at least two polynucleotides such that the at least two polynucleotides are inherited together in more than 50% of meioses, i.e., not randomly. Accordingly, when a plant or plant cell comprising stacked expression cassettes with two polynucleotides undergoes meiosis, the two polynucleotides segregate into the same progeny (daughter) cell. In this manner, stacked polynucleotides will likely be expressed together in any cell for which they are present. For example, a plant may comprise an expression cassette comprising a male fertility polynucleotide stacked with an expression cassette comprising a male-gamete-disruptive polynucleotide such that the male fertility polynucleotide and the male-gamete-disruptive polynucleotide are inherited together. Specifically, a male sterile plant could comprise an expression cassette comprising a male fertility polynucleotide disclosed herein operably linked to a constitutive promoter, stacked with an expression cassette comprising a male-gamete-disruptive polynucleotide operably linked to a male tissue-preferred promoter, such that the plant produces mature pollen grains. However, in such a plant, development of the daughter pollen cells comprising the male fertility polynucleotide will be prevented by expression of the male-gamete-disruptive polynucleotide.

B. Plants and Methods of Introduction

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein "grain" is intended the mature seed produced by commercial growers for purposes other than growing or reproducing the species. Progeny, variants, and mutants of the regenerated plants are also included within the scope of the disclosure, provided that these parts comprise the introduced nucleic acid sequences.

The methods disclosed herein comprise introducing a polypeptide or polynucleotide into a plant cell. "Introducing" is intended to mean presenting to the plant the polynucleotide or polypeptide in such a manner that the sequence gains access to the interior of a cell. The methods disclosed herein do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof "Transient transformation" is intended to mean that a polynucleotide is introduced into the host (i.e., a plant) and expressed temporally or a polypeptide is introduced into a host (i.e., a plant).

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci.* USA 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the male fertility polynucleotides or expression cassettes disclosed herein can be provided to a plant using a variety of transient transformation methods. Such transient transformation methods include, but are not limited to, the introduction of the male fertility polypeptide or variants and fragments thereof directly into the plant or the introduction of a male fertility transcript into the plant. Such methods include, for example, microinjection or particle bombardment. See, for example, Crossway et al. (1986)*Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the male fertility polynucleotide or expression cassettes disclosed herein can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the male fertility polynucleotides or expression cassettes disclosed herein may be introduced into plants by contacting plants with a virus or viral nucleic acids. Generally, such methods involve incorporating a nucleotide construct of disclosed herein within a viral DNA or RNA molecule. It is recognized that a male fertility sequence disclosed herein may be initially synthesized as part of a viral polyprotein, which later may be processed by proteolysis in vivo or in vitro to produce the desired recombinant protein. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference.

Briefly, the polynucleotide disclosed herein can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and pollinated with either the same transformed strain or different strains, and the resulting progeny having desired expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a male fertility polynucleotide disclosed herein, for example, an expression cassette disclosed herein, stably incorporated into their genome. Seed comprising any expression cassette disclosed herein can be sorted based on size parameters, including but not limited to, seed length, seed width, seed density, or any combination thereof.

The male fertility polynucleotides and expression cassettes disclosed herein may be used for transformation of any plant species, including, but not limited to, monocots and dicots. Examples of plant species of interest include, but are not limited to, corn (*Zea mays*), *Brassica* sp. (e.g., *B. napus, B. raga, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, grasses and conifers.

In particular embodiments, wheat plants are used in the methods and compositions disclosed herein. As used herein, the term "wheat" refers to any species of the genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. mocha, T. compactum, T. sphaerococcum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-*Triticum* species, such as rye *Secale cereale*, including but not limited to Triticale. In some embodiments, the wheat plant is suitable for commercial production of grain, such as commercial varieties of hexaploid wheat or durum wheat, having suitable agronomic characteristics which are known to those skilled in the art.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*.

Conifers that may be employed in practicing the present methods and compositions include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants disclosed herein are crop plants (for example, corn, alfalfa, sunflower, *Brassica*, soybean, cotton, safflower, peanut, *sorghum*, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica, maize*, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of the methods and compositions disclosed herein to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein disclosed herein are available using *Bacillus* sp. and *Salmonella* (Palva et al. (1983) *Gene* 22:229-235); Mosbach et al. (1983) *Nature* 302:543-545).

In some embodiments, the expression cassette or male fertility polynucleotides disclosed herein are maintained in a hemizygous state in a plant. Hemizygosity is a genetic condition existing when there is only one copy of a gene (or set of genes) with no allelic counterpart on the sister chromosome. In certain embodiments, the expression cassettes disclosed herein comprise a first promoter operably linked to a male fertility polynucleotide which is stacked with a male-gamete-disruptive polynucleotide operably linked to a male tissue-preferred promoter, and such expression cassettes are introduced into a male sterile plant in a hemizygous condition. When the male fertility polynucleotide is expressed, the plant is able to successfully produce mature pollen grains because the male fertility polynucleotide restores the plant to a fertile condition. Given the hemizygous condition of the expression cassette, only certain daughter cells will inherit the expression cassette in the process of pollen grain formation. The daughter cells that inherit the expression cassette containing the male fertility polynucleotide will not develop into mature pollen grains due to the male tissue-preferred expression of the stacked encoded male-gamete-disruptive gene product. Those pollen grains that do not inherit the expression cassette will continue to develop into mature pollen grains and be functional, but will not contain the male fertility polynucleotide of the expression cassette and therefore will not transmit the male fertility polynucleotide to progeny through pollen.

V. Modulating the Concentration and/or Activity of Male Fertility Polypeptides

A method for modulating the concentration and/or activity of the male fertility polypeptides disclosed herein in a plant is provided. The term "influences" or "modulates", as used herein with reference to the concentration and/or activity of the male fertility polypeptides, refers to any increase or decrease in the concentration and/or activity of the male fertility polypeptides when compared to an appropriate control. In general, concentration and/or activity of a male fertility polypeptide disclosed herein is increased or decreased by at least 1%, 5%, 10%, 20%, 30%, 40%, 50%, 60%, 70%, 80%, or 90% relative to a native control plant, plant part, or cell. Modulation as disclosed herein may occur during and/or subsequent to growth of the plant to the desired stage of development. In specific embodiments, the male fertility polypeptides disclosed herein are modulated in monocots, particularly wheat.

A variety of methods can be employed to assay for modulation in the concentration and/or activity of a male fertility polypeptide. For instance, the expression level of the male fertility polypeptide may be measured directly, for example, by assaying for the level of the male fertility polypeptide in the plant (i.e., Western or Northern blot), or indirectly, for example, by assaying the male fertility activity of the male fertility polypeptide in the plant. Methods for measuring the male fertility activity are described elsewhere herein. In specific embodiments, modulation of male fertility polypeptide concentration and/or activity comprises the modulation (i.e., an increase or a decrease) in the level of male fertility polypeptide in the plant. Methods to measure the level and/or activity of male fertility polypeptides are known in the art and are discussed elsewhere herein. In still other embodiments, the level and/or activity of the male fertility polypeptide is modulated in vegetative tissue, in reproductive tissue, or in both vegetative and reproductive tissue.

In one embodiment, the activity and/or concentration of the male fertility polypeptide is increased by introducing the polypeptide or the corresponding male fertility polynucleotide into the plant. Subsequently, a plant having the introduced male fertility sequence is selected using methods known to those of skill in the art such as, but not limited to, Southern blot analysis, DNA sequencing, PCR analysis, or phenotypic analysis. In certain embodiments, marker polynucleotides are introduced with the male fertility polynucleotide to aid in selection of a plant having or lacking the male fertility polynucleotide disclosed herein. A plant or plant part altered or modified by the foregoing embodiments is grown under plant forming conditions for a time sufficient to modulate the concentration and/or activity of the male fertility polypeptide in the plant. Plant forming conditions are well known in the art.

As discussed elsewhere herein, many methods are known the art for providing a polypeptide to a plant including, but not limited to, direct introduction of the polypeptide into the plant, or introducing into the plant (transiently or stably) a polynucleotide construct encoding a male fertility polypeptide. It is also recognized that the methods disclosed herein may employ a polynucleotide that is not capable of directing, in the transformed plant, the expression of a protein or an RNA. Thus, the level and/or activity of a male fertility polypeptide may be increased by altering the gene encoding the male fertility polypeptide or its promoter. See, e.g., Kmiec, U.S. Pat. No. 5,565,350; Zarling et al., PCT/US93/03868. Therefore mutagenized plants that carry mutations in male fertility genes, where the mutations increase expression of the male fertility gene or increase the activity of the encoded male fertility polypeptide are provided.

In other embodiments, the concentration and/or activity of a male fertility polypeptide is increased by introduction into a plant of an expression cassette comprising a male fertility polynucleotide (e.g. SEQ ID NO: 1, 3, 5, 7, 9, 11, 13, 15, or 17), or an active fragment or variant thereof, as disclosed elsewhere herein. The male fertility polynucleotide may be operably linked to promoter that is heterologous to the plant or native to the plant. By increasing the concentration and/or activity of a male fertility polypeptide in a plant, the male fertility of the plant is likewise increased. Thus, the male fertility of a plant can be increased by increasing the concentration and/or activity of a male fertility polypeptide. For example, male fertility can be restored to a male sterile plant by increasing the concentration and/or activity of a male fertility polypeptide.

It is also recognized that the level and/or activity of the polypeptide may be modulated by employing a polynucleotide that is not capable of directing, in a transformed plant, the expression of a protein or an RNA. For example, the polynucleotides disclosed herein may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference. It is therefore recognized that methods disclosed herein do not depend on the incorporation of the entire polynucleotide into the genome, only that the plant or cell thereof is altered as a result of the introduction of the polynucleotide into a cell.

In one embodiment, the genome may be altered following the introduction of the polynucleotide into a cell. For example, the polynucleotide, or any part thereof, may incorporate into the genome of the plant. Alterations to the genome disclosed herein include, but are not limited to, additions, deletions, and substitutions of nucleotides into the genome. While the methods disclosed herein do not depend on additions, deletions, and substitutions of any particular number of nucleotides, it is recognized that such additions, deletions, or substitutions comprises at least one nucleotide.

TABLE 1

Summary of SEQ ID NOS

| SEQ ID: | Description |
|---|---|
| 1 | Wheat (*T. urartu*, A genome) Ms22 polynucleotide |
| 2 | Wheat (*T. urartu*, A genome) Ms22 polypeptide |
| 3 | Wheat (*Ae. Speltoides*, B genome) Ms22 polynucleotide |
| 4 | Wheat (*Ae. Speltoides*, B genome) Ms22 polypeptide |
| 5 | Wheat (*Ae. Tauschii*, D genome) Ms22 polynucleotide |
| 6 | Wheat (*Ae. Tauschii*, D genome) Ms22 polypeptide |
| 7 | Wheat (*T. urartu*, A genome) Ms26 polynucleotide |
| 8 | Wheat (*T. urartu*, A genome) Ms26 polypeptide |
| 9 | Wheat (*Ae. Speltoides*, B genome) Ms26 polynucleotide |
| 10 | Wheat (*Ae. Speltoides*, B genome) Ms26 polypeptide |
| 11 | Wheat (*Ae. Tauschii*, D genome) Ms26 polynucleotide |
| 12 | Wheat (*Ae. Tauschii*, D genome) Ms26 polypeptide |
| 13 | Wheat (*T. urartu*, A genome) Ms45 polynucleotide |
| 14 | Wheat (*T. urartu*, A genome) Ms45 polypeptide |
| 15 | Wheat (*Ae. Speltoides*, B genome) Ms45 polynucleotide |
| 16 | Wheat (*Ae. Spehoides*, B genome) Ms45 polypeptide |
| 17 | Wheat (*Ae. Tauschii*, D genome) Ms45 polynucleotide |
| 18 | Wheat (*Ae. Tauschii*, D genome) Ms45 polypeptide |
| 19 | Heme-binding domain of Ms26: FxxGxRxCxG |
| 20 | Dioxygen binding domain A of Ms26 A/GGXD/ETT/S |
| 21 | MS26+ target site |
| 22-27 | primers |
| 28 | Wheat A genome, FIG. 1 |
| 29 | Wheat B genome, FIG. 1 |
| 30 | Wheat D genome, FIG. 1 |
| 31 | Maize MS26, FIG. 1 |
| 32 | *Sorghum* MS26, FIG. 1 |
| 33 | Rice MS26, FIG. 1 |
| 34-44 | See FIG. 2 description |
| 45-52 | See FIG. 4 description |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1. Identification of Male Fertility Polynucleotides in Wheat

Male-fertility polynucleotides disclosed herein may be identified using bioinformatic approaches. As an example, sequences putatively representing male-fertility genes in wheat are initially identified by an in silico search of proprietary databases using known fertility genes from other species, such as maize. Candidate ESTs are selected based on protein-level homology to the reference sequences and consideration of the library from which the candidate sequence originated, e.g. representing expression in male reproductive tissue.

Based on the candidate EST sequences, primers are created and used to screen a proprietary wheat BAC library. Super-pools identified are further screened with appropriate primers to identify specific BAC clones comprising the ESTs.

Touchdown PCR may be performed (GeneAmp® PCR System 9700, Applied Biosystems), using the following cycling parameters: 94° C. for 3 min (one cycle), 94° C. for 1 min, 55° C. for 1 min and 72° C. for 1 min 30 s, (35 cycles), 72° C. for 7 min, and termination at 4° C. Pfu Ultra Hotstart™ DNA polymerase (Stratagene) may be preferred for its very low average error rate (less than 0.5% per 500-bp fragment amplified).

Wheat insert DNA isolated from the BAC clones is digested for Southern blot confirmation using a candidate EST clone as a probe. BAC fragments are subcloned into pBluescript® (Stratagene Inc., La Jolla, CA). White colonies are grown in LB medium and transferred onto a membrane using a dot-blot procedure. After denaturation the membrane is probed with a candidate EST clone. Positive clones are identified and sequenced.

Example 2. Comparison of Wheat Male Fertility Polynucleotide with Known Sequences

TABLE 2

Global Identity of Wheat, Maize, and Rice Ms22 Polynucleotides and Polypeptides

| MS22 | T urartu A genome | Ae speltoides B genome | Ae tauschii D genome | Maize ms22 | Rice ms22 |
|---|---|---|---|---|---|
| T urartu A genome | | 97.6* | 99.0* | 79.9* | 81.0* |
| Ae speltoides B genome | 98.5 | | 98.1* | 79.6* | 81.0* |
| Ae tauschii D genome | 98.5 | 98.5 | | 79.6* | 81.5* |
| Maize ms22 | 89.2 | 89.2 | 89.2 | | 83.6* |
| Rice ms22 | 86.2 | 86.2 | 81.9 | 78.0 | |

(Polynucleotide result is listed with an asterisk; polypeptide result is listed wit rout an asterisk.)

TABLE 3

Global Identity of Wheat, Maize, and Rice Ms26 Polynucleotides and Polypeptides

| MS26 | T urartu A genome | Ae speltoides B genome | Ae tauschii D genome | Maize ms26 | Rice ms26 |
|---|---|---|---|---|---|
| T urartu A genome |  | 97.7* | 97.9* | 82.1* | 81.8* |
| Ae speltoides B genome | 99.1 |  | 97.9* | 82.2* | 82.3* |
| Ae tauschii D genome | 98.9 | 99.1 |  | 82.0* | 82.8* |
| Maize ms26 | 89.0 | 89.0 | 88.8 |  | 80.5* |
| Rice ms26 | 90.4 | 90.5 | 90.2 | 87.7 |  |

(Polynucleotide result is listed with an asterisk; polypeptide result is listed without an asterisk.)

TABLE 4

Global Identity of Wheat, Maize, and Rice Ms45 Polynucleotides and Polypeptides

| MS45 | T urartu A genome | Ae speltoides B genome | Ae tauschii D genome | Maize ms45 | Rice ms45 |
|---|---|---|---|---|---|
| T urartu A genome |  | 96.3* | 98.5* | 79.5* | 78.0* |
| Ae speltoides B genome | 99.3 |  | 96.7* | 79.1* | 78.6* |
| Ae tauschii D genome | 99.5 | 99.3 |  | 78.6* | 78.9* |
| Maize ms45 | 81.6 | 81.8 | 81.1 |  | 76.9* |
| Rice ms45 | 85.0 | 84.7 | 84.7 | 82.8 |  |

(Polynucleotide result is listed with an asterisk; polypeptide result is listed without an asterisk.)

Example 3. Wheat Transformation

Wheat transformation protocols are available to one of skill in the art. See, for example, He et al. (2010) *J. Exp. Botany* 61(6):1567-1581; Wu et al. (2008) *Transgenic Res.* 17:425-436; Nehra et al. (1994) *Plant J.* 5(2):285-297; Rasco-Gaunt et al. (2001) *J. Exp. Botany* 52(357):865-874; Razzaq et al. (2011) *African J Biotech.* 10(5):740-750.

Example 4. Directed Modification of MS26

This example describes methods to mutate wheat genes using double-strand-break technologies to enable directed DNA modification or gene insertion via homologous recombination. More specifically, this example describes a method which includes, but is not limited to, delivery of a custom homing endonuclease, MS26+, to recognize, cleave, and mutate wheat chromosomal DNA through imprecise non-homologous end-joining (NHEJ) repair.

Vectors and Transformation:

Male fertility MS26 genes located within wheat genomes A, B and D contain a 22 base pair sequence (5'-GATGGTGACGTACGTGCCCTAC-3'; SEQ ID NO: 21) which is recognized by an MS26+ homing endonuclease as a substrate for introducing a double strand break. The 22 bp MS26 recognition site is present within the A, B and D wheat genomes and conserved across maize, *sorghum* and rice MS26 orthologous genes (FIG. 1). The MS26+ homing endonuclease has been shown to generate mutations in maize, rice and *sorghum* plants WO2013/066423, published on May 10, 2013. To generate mutations in the genomic Ms26 genes in wheat plants, PHP42063 was introduced into wheat Fielder variety by *Agrobacterium*-mediated transformation methods similar to those described (Tamas-Nyitrai et al Plant Cell Cultures Protocols Methods in Molecular Biology 877, 2012, 357-384; He, et al., (2010) *J. Exp. Botany* 61(6):1567-1581; Wu, et al., (2008) *Transgenic Res.* 17:425-436; Nehra, et al., (1994) *Plant J.* 5(2):285-297; Rasco-Gaunt, et al., (2001) *J. Exp. Botany* 52(357):865-874; Razzaq, et al., (2011) *African J. Biotech.* 10(5):740-750).

PHP42063 contains a single chain MS26+ placed under the transcriptional control of the maize CAS1 promoter. The CAS1 promoter can be transcriptionally induced by either the sulfonylurea-safener, 2-CBSU, or by elevated temperature (U.S. patent application Ser. No. 13/896,437 filed May 17, 2013). PHP42063 also contains a blue-fluorescence gene (CFP) regulated by the ZmEND2 promoter which is used as visual marker for the selection of integration of the T-DNA into wheat cells. In addition, PHP42063 contains a copy of a red fluorescence gene regulated by the maize Histone 2B promoter. A portion of the red fluorescence gene in this construct was duplicated in a direct orientation, consisting of two fragments of the RFP gene with 369 bp of overlap. The two fragments are separated by a 136-bp spacer containing an MS26 target site. Blue fluorescing calli were selected and used for regeneration of wheat plants and grown in the greenhouse to maturity and seed set. Wheat plants containing TDNA insertions of PHP42063 were verified by copy-number analysis. Four independent single or low-copy PHP42063 transformed plants were selected for additional experimentation. Blue fluorescing immature embryos were harvested 14-20 days after pollination, sterilized, placed on maintenance media and incubated in the dark at 37 C for 24 hours. At the end of this period, embryos incubated at the elevated temperature were moved to room temperature (<26C) and embryos were allowed to grow in the dark. Approximately 72 hours after the initiation of treatment at elevated temperature, embryos incubated at 37 C begin to develop red fluorescing sectors. This observation suggests that the heat inducible gene cassette, CAS1:MS26+, has resulted in double-strand-breaks at the MS26 target site between the two overlapping sequences of the RF-FP reporter, promoting intramolecular recombination and producing a functional RFP gene which is revealed by the appearance of red fluorescing cells against a background of blue fluorescence. Red fluorescing callus events were selected for additional molecular characterization and plant regeneration.

Identification of Mutations at the TaMS26 Target Site in Plant Tissues.

Total genomic DNA was extracted from the heat treated and non-heat treated callus transformed with the MS26+ homing endonuclease and the region surrounding the genomic target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 5.

TABLE 5

PCR primer sequences

| Target Site | Primer Orientation | Primary PCR Primer Sequence | SEQ ID NO: |
|---|---|---|---|
| MS26+ Homing Endonuclease | Forward | CTACACTCTTTCCCTACACG ACGCTCTTCCGATCTAACCC GCGGAGGACGACGTGCTC | 22 |
| MS26+ Homing Endonuclease | Reverse | CAAGCAGAAGACGGCATACG AGCTCTTCCGATCTCGTCGG GGCCCCAGTTGTAC | 23 |

The primers used in the secondary PCR reaction were AATGATACGGCGACCACCGAGATCTA-CACTCTTTCCCTACACG (forward, SEQ ID NO: 24) and CAAGCAGAAGACGGCATA (reverse, SEQ ID NO: 25). Genomic DNA extracted from leaves of untransformed Fielder plants served as a negative control.

The resulting PCR amplifications were concentrated using a Qiagen Minielute PCR purification spin column, electrophoresed on a 2% agarose gel and the appropriate amplifications were excised and purified with a Qiagen Gel Extraction spin column. The concentration of the gel purified amplifications was measured with a Hoechst dye-based fluorometric assay, combined in an equimolar ratio, and single read 100 nucleotide-length deep sequencing was performed on Illumina's Genome Analyzer IIx (ELIM Biopharmaceuticals, Inc.) with a 30-40% (v/v) spike of PhiX control v3 (Illumina, FC-110-3001) to off-set sequence bias. Only those reads with a ≥1 nucleotide indel arising within a 6 nucleotide window centered over the expected site of cleavage and not found in a similar level in the negative control were classified as NHEJ mutations. The total numbers of NHEJ mutations were then used to calculate the % mutant reads based on the total number of reads of an appropriate length containing a perfect match to the barcode and forward primer.

The frequency of NHEJ mutations recovered by deep sequencing for the non-heat treated and heat treated callus transformed with the MS26+ homing endonuclease compared to the negative control is shown in Table 6. The ten most prevalent types of NHEJ mutations recovered from the heat treated callus are shown in FIG. 2. These data suggest that the MS26+ homing endonuclease effectively introduced NHEJ mutations and alterations into the native MS26 wheat genes.

TABLE 6

Percent (%) mutant reads at the wheat MS26+ homing endonuclease target locus.

| System | Total Number of Mutant Reads | Total Number of Reads | % Mutant Reads |
| --- | --- | --- | --- |
| Untransformed Wheat Genomic DNA Control | 19 | 3,989,749 | 0.00% |
| Wheat Callus Transformed with MS26+ Homing Endonuclease (No Heat Treatment) | 304 | 4,069,593 | 0.007% |

TABLE 6-continued

Percent (%) mutant reads at the wheat MS26+ homing endonuclease target locus.

| System | Total Number of Mutant Reads | Total Number of Reads | % Mutant Reads |
| --- | --- | --- | --- |
| Wheat Callus Transformed with MS26+ Homing Endonuclease (37C for 24 hours) | 64,158 | 4,055,925 | 1.58% |

Identification of Mutations at the TaMS26 Target Site in Regenerated Plants.

Red-fluorescing callus events were selected for plant regeneration. Plants were grown in the greenhouse and leaf DNA from individual regenerated wheat plants (n=122) was screened for MS26-1 target site mutations by amplification of the region by PCR using the primer pair UNIMS26 5'-2 (GACGTGGTGCTCAACTTCGTGAT; SEQ ID NO: 26) and UNIMS26 3'-1 (GCCATGGAGAGGATGGTCATCAT; SEQ ID NO: 27) and digestion of the amplified products with the DNA restriction enzyme, BsiWI, which recognizes the sequence 5'-CGTACG-3'. Products of these reactions were electrophoresed on 1% agarose gels and screened for BsiWI digestion resistant bands indicative of mutations at the MS26-1 targets site.

Ten out of the 122 regenerated plants screened from PHP42063 heat treated embryos contained PCR products resistant to BsiWI restriction enzyme digestion indicating mutations at the MS26 target site. Subcloning and DNA sequence analysis of these PCR products revealed a variety of mutations across the MS26 target site ranging from a single nucleotide insertion to deletions of 4 to 98 nucleotides. In total, seven non-identical mutations were identified in these regenerated wheat plants (FIG. 3). Plants containing these mutations were allowed to self-pollinate. Progeny plants were screened for meiotic inheritance of the above describe mutations by PCR amplification to reveal BsiWI digestion resistant bands indicative of mutations at the MS26-1 targets site (as describe above). BsiWI resistant PCR amplification products were identified in progeny plants grown from selfed seed derived parent plants which contained mutant Ms26 alleles, while DNA sequence analysis of these products confirmed sexual transmission of the original mutation to the next generation.

This example demonstrates the modification of wheat genes by directed delivery of a double-strand-break reagent, in this case a custom homing endonuclease, which recognized, cleaved, and mutated wheat chromosomal DNA through end-joining repair.

That which is claimed:

1. A method of restoring male fertility to a mutated MS45 male-sterile wheat plant, wherein said method comprises introducing into said wheat plant a polynucleotide operably linked to a promoter that drives expression in a wheat plant, said polynucleotide comprising a nucleotide sequence selected from the group consisting of:
   (a) a nucleotide sequence comprising SEQ ID NO: 13; and
   (b) a nucleotide sequence comprising at least 95% sequence identity to SEQ ID NO: 13; and
expressing said polynucleotide in the wheat plant to confer male fertility to the mutated MS45 male-sterile wheat plant, wherein said polynucleotide is linked to a heterologous polynucleotide encoding a marker.

2. The method of claim 1, wherein said promoter is a constitutive promoter, inducible promoter, tissue-preferred promoter, or growth stage-preferred promoter.

3. The method of claim 2, wherein said tissue-preferred promoter is a male tissue-preferred promoter.

4. The method of claim 1, wherein the marker is a color marker.

5. The method of claim 1, wherein the marker is a screenable or scorable marker.

6. The method of claim 5, wherein the screenable marker is a pigment.

7. The method of claim 5, wherein the screenable marker is an anthocyanin or a flavonoid.

* * * * *

SEQUENCE LISTING

<160> NUMBER OF SEQ ID NOS: 52

<210> SEQ ID NO 1
<211> LENGTH: 414
<212> TYPE: DNA
<213> ORGANISM: Triticum urartu

<400> SEQUENCE: 1

```
atgttgagga tgcagcagca ggtggagggc gtggtgggcg gcggcatcgt ggccgaggcg      60
gaggaggcgg cggtgtacga gcgggtggct cgcatggcca gcggcaacgc ggtggtcgtc     120
ttcagcgccm gcggctgctg catgtgccac gtcgtcaagc gcctcctgct tggcctgggg     180
gtcggcccca ccgtctacga gttggaccag atgggcggcg ccgggcgaga gatccaggcg     240
```

```
gcgctggcgc agctgctgcc ccccggaccc ggcgccggcc accaccagca gccgccagtg    300
cccgtggtgt tcgtcggcgg gaggctcctg ggcggcgtgg agaaggtcat ggcgtgccac    360
atcaacggca cgctcgtccc gctcctcaag gacgccggcg cgctctggct ctga           414
```

<210> SEQ ID NO 2
<211> LENGTH: 137
<212> TYPE: PRT
<213> ORGANISM: Triticum urartu
<220> FEATURE:
<221> NAME/KEY: misc_feature
<223> OTHER INFORMATION: Xaa = any amino acid
<220> FEATURE:
<221> NAME/KEY: misc_feature
<222> LOCATION: (44)..(44)
<223> OTHER INFORMATION: Xaa can be any naturally occurring amino acid

<400> SEQUENCE: 2

```
Met Leu Arg Met Gln Gln Val Glu Gly Val Val Gly Gly Gly Ile
1               5                   10                  15

Val Ala Glu Ala Glu Ala Ala Val Tyr Glu Arg Val Ala Arg Met
            20                  25                  30

Ala Ser Gly Asn Ala Val Val Val Phe Ser Ala Xaa Gly Cys Cys Met
        35                  40                  45

Cys His Val Val Lys Arg Leu Leu Leu Gly Leu Gly Val Gly Pro Thr
    50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
                85                  90                  95

Gln Pro Pro Val Pro Val Val Phe Val Gly Gly Arg Leu Leu Gly Gly
            100                 105                 110

Val Glu Lys Val Met Ala Cys His Ile Asn Gly Thr Leu Val Pro Leu
        115                 120                 125

Leu Lys Asp Ala Gly Ala Leu Trp Leu
    130                 135
```

<210> SEQ ID NO 3
<211> LENGTH: 414
<212> TYPE: DNA
<213> ORGANISM: Aegilops speltoides

<400> SEQUENCE: 3

```
atgttgagga tgcagcagca ggtggagggc gtggtgggcg gcggcatcgt ggcggaggcg     60
gaggaggcgg ccgtgtacga gcgggtggct cgcatggcca gcggcaacgc ggtggtcgtc    120
ttcagcgcca gcggctgctg catgtgccac gtcgtcaagc gcctcctgct tggcctggga    180
gtcggcccca ccgtgtacga gttggaccag atgggcggcg ccgggcggga gatccaggcg    240
gccctggcgc agctgctgcc ccccggaccc ggcgccggcc accaccagca gccgccggtg    300
cccgtggtgt tcgtyggcgg gaggctcctg ggcggcgtgg agaaggtgat ggcgtgccac    360
atcaacggca cgctcgtccc gctcctcaag gacgccggcg cgctctggct ctga           414
```

<210> SEQ ID NO 4
<211> LENGTH: 137
<212> TYPE: PRT
<213> ORGANISM: Aegilops speltoides
<220> FEATURE:
<221> NAME/KEY: misc_feature
<223> OTHER INFORMATION: Xaa = any amino acid
<220> FEATURE:

<221> NAME/KEY: misc_feature
<222> LOCATION: (105)..(105)
<223> OTHER INFORMATION: Xaa can be any naturally occurring amino acid

<400> SEQUENCE: 4

```
Met Leu Arg Met Gln Gln Gln Val Glu Gly Val Val Gly Gly Gly Ile
1               5                   10                  15

Val Ala Glu Ala Glu Glu Ala Ala Val Tyr Glu Arg Val Ala Arg Met
            20                  25                  30

Ala Ser Gly Asn Ala Val Val Phe Ser Ala Ser Gly Cys Cys Met
        35                  40                  45

Cys His Val Val Lys Arg Leu Leu Gly Leu Gly Val Gly Pro Thr
50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
            85                  90                  95

Gln Pro Pro Val Pro Val Val Phe Xaa Gly Gly Arg Leu Leu Gly Gly
            100                 105                 110

Val Glu Lys Val Met Ala Cys His Ile Asn Gly Thr Leu Val Pro Leu
            115                 120                 125

Leu Lys Asp Ala Gly Ala Leu Trp Leu
            130                 135
```

<210> SEQ ID NO 5
<211> LENGTH: 414
<212> TYPE: DNA
<213> ORGANISM: Aegilopsm tauschii

<400> SEQUENCE: 5

```
atgttgagga tgcagcagca ggtggagggc gtggtgggcg gcggcatcat ggcggaggcg    60
gaggaggcgg cggtgtacga gcgggtggct cgcatggcca gcggcaacgc ggtggtcgtc   120
ttcagcgcca gcggctgctg catgtgccac gtcgtcaagc gcctcctgct tggcctgggg   180
gtcggcccca ccgtctacga gttggaccag atgggcggcg ccgggcgaga gatccaggcg   240
gcgctggcgc agctgctgcc ccccggaccc ggcgccggcc accaccagca gccgccagtg   300
cccgtggtgt tcgtcggcgg gaggctcctg ggcggcgtgg agaaggtgat ggcgtgccac   360
atcaacggca cgctcgtccc gctcctcaag gacgccggcg cgctctggct ctga         414
```

<210> SEQ ID NO 6
<211> LENGTH: 137
<212> TYPE: PRT
<213> ORGANISM: Aegilops tauschii

<400> SEQUENCE: 6

```
Met Leu Arg Met Gln Gln Gln Val Glu Gly Val Val Gly Gly Gly Ile
1               5                   10                  15

Met Ala Glu Ala Glu Glu Ala Ala Val Tyr Glu Arg Val Ala Arg Met
            20                  25                  30

Ala Ser Gly Asn Ala Val Val Val Phe Ser Ala Ser Gly Cys Cys Met
        35                  40                  45

Cys His Val Val Lys Arg Leu Leu Gly Leu Gly Val Gly Pro Thr
50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
```

```
                    85                  90                  95
       Gln Pro Pro Val Pro Val Val Phe Val Gly Gly Arg Leu Leu Gly Gly
                100                 105                 110

Val Glu Lys Val Met Ala Cys His Ile Asn Gly Thr Leu Val Pro Leu
                115                 120                 125

Leu Lys Asp Ala Gly Ala Leu Trp Leu
                130                 135

<210> SEQ ID NO 7
<211> LENGTH: 1934
<212> TYPE: DNA
<213> ORGANISM: Triticum urartu

<400> SEQUENCE: 7
atggaggaag ctcacggcgg catgccgtcg acgacgacgg cgttcttccc gctggcaggg      60
ctccacaagt tcatggccat cttcctcgtg ttcctctcgt ggatcttggt ccactggtgg     120
agcctgagga agcagaaggg gccgaggtca tggccggtca tcggcgcgac gctggagcag     180
ctgaggaact actaccggat gcacgactgg ctcgtggagt acctgtccaa gcaccggacg     240
gtcaccgtcg acatgccctt cacctcctac acctacatcg ccgaccccgt gaacgtcgag     300
catgtgctca agaccaattt caacaattac cccaaggtga acaatcctc gagatgtcag     360 acaaggttca gtaatcggta ctgacagtgt tacaaatgtc tgaaatctga aattgtatgt     420 ctaggggag gtgtacaggt cctacatgga cgtgctgctc ggcgacggca tattcaacgc     480
cgacggcgag ctctggagga agcagaggaa cggcgagc ttcgagttcg cttccaagaa     540
cctgagagac ttcagcacga tcgtgttcag ggagtactcg ctgaagctgt ccagcatcct     600
gagccaggct tgcaaggccg gcaaagtcgt ggacatgcag gcaactgaac tcattccctt     660
ggtcatctga acgttgattt cttggacaaa atttcaagat tctgacgcga gcggacgaat     720
tcaggagctg tacatgagga tgacgctgga ctcgatctgc aaggtcgggt tcggggtcga     780
gatcggcacg ctgtcgccgg agctgccgga gaacagcttc gcgcaggcgt tcgacgccgc     840
caacatcatc gtgacgctgc ggttcatcga cccgctgtgg cgcgtgaaga agttcctgca     900
cgtcggctcg gaggcgctgc tggagcagag catcaagctc gtcgacgagt tcacctacag     960
cgtcatccgc cggcgcaagg ccgagatcgt gcaggcccgg ccagcggca agcaggagaa    1020 ggtgcgtgcg tgatcatcgt cattcgtcaa gctccggatc gctggtttgt gtagtaggtg    1080
ccattgatca ctgacacgtt aactgggtgc gcagatcaag cacgacatac tgtcgcggtt    1140
catcgagctg ggcgaggccg gcggcgacga cggcggcagc ctgttcgggg acgacaaggg    1200
cctccgcgac gtggtgctca acttcgtgat cgccgggcgg gacaccacgg ccacgacgct    1260
gtcctggttc acctacatgg ccatgacgca cccggccgtg gccgagaagc tccgccgcga    1320
gctggccgcc ttcgaggcgg atcgcgcccg cgaggagggc gtcgctctgg tccctgcag    1380 cgacggcgag ggcgccgacg aggccttcgc cgcccgcgtg gcgcagttcg cggggctcct    1440
gagctacgac gggctcggga agctggtgta cctccacgcg tgcgtgacgg agacgctgcg    1500
gctgtacccg gcggtgccgc aggaccccaa gggcatcgcg gaggacgacg tgctcccgga    1560
cggcaccaag gtgcgcgccg gcgggatggt gacgtacgtg ccctactcca tggggcggat    1620
ggagtataac tggggccccg acgccgccag cttccggccg gagcggtgga tcggcgacga    1680
cggcgcgttc gcaacgcgt cgccgttcaa gttcacggcg ttccaggcgg ggccgcggat    1740
ctgcctcggc aaggactcgg cgtacctgca gatgaagatg gcgctggcca tactgtgcag    1800
```

```
gttcttcagg ttcgagctcg tggagggcca ccccgtcaag taccgcatga tgaccatcct    1860
ctccatggcg cacggcctca aggtccgcgt ctccagggcg ccgctcgcct gatcttgatc    1920
tgggttccgg cgag                                                       1934
```

<210> SEQ ID NO 8
<211> LENGTH: 548
<212> TYPE: PRT
<213> ORGANISM: Triticum urartu

<400> SEQUENCE: 8

```
Met Glu Glu Ala His Gly Gly Met Pro Ser Thr Thr Ala Phe Phe
1               5                   10                  15

Pro Leu Ala Gly Leu His Lys Phe Met Ala Ile Phe Leu Val Phe Leu
                20                  25                  30

Ser Trp Ile Leu Val His Trp Trp Ser Leu Arg Lys Gln Lys Gly Pro
            35                  40                  45

Arg Ser Trp Pro Val Ile Gly Ala Thr Leu Glu Gln Leu Arg Asn Tyr
        50                  55                  60

Tyr Arg Met His Asp Trp Leu Val Glu Tyr Leu Ser Lys His Arg Thr
65                  70                  75                  80

Val Thr Val Asp Met Pro Phe Thr Ser Tyr Thr Ile Ala Asp Pro
                85                  90                  95

Val Asn Val Glu His Val Leu Lys Thr Asn Phe Asn Asn Tyr Pro Lys
            100                 105                 110

Gly Glu Val Tyr Arg Ser Tyr Met Asp Val Leu Leu Gly Asp Gly Ile
        115                 120                 125

Phe Asn Ala Asp Gly Glu Leu Trp Arg Lys Gln Arg Lys Thr Ala Ser
130                 135                 140

Phe Glu Phe Ala Ser Lys Asn Leu Arg Asp Phe Ser Thr Ile Val Phe
145                 150                 155                 160

Arg Glu Tyr Ser Leu Lys Leu Ser Ser Ile Leu Ser Gln Ala Cys Lys
                165                 170                 175

Ala Gly Lys Val Val Asp Met Gln Glu Leu Tyr Met Arg Met Thr Leu
            180                 185                 190

Asp Ser Ile Cys Lys Val Gly Phe Gly Val Glu Ile Gly Thr Leu Ser
        195                 200                 205

Pro Glu Leu Pro Glu Asn Ser Phe Ala Gln Ala Phe Asp Ala Ala Asn
    210                 215                 220

Ile Ile Val Thr Leu Arg Phe Ile Asp Pro Leu Trp Arg Val Lys Lys
225                 230                 235                 240

Phe Leu His Val Gly Ser Glu Ala Leu Leu Glu Gln Ser Ile Lys Leu
                245                 250                 255

Val Asp Glu Phe Thr Tyr Ser Val Ile Arg Arg Lys Ala Glu Ile
            260                 265                 270

Val Gln Ala Arg Ala Ser Gly Lys Gln Glu Lys Ile Lys His Asp Ile
        275                 280                 285

Leu Ser Arg Phe Ile Glu Leu Gly Glu Ala Gly Gly Asp Gly Gly
    290                 295                 300

Ser Leu Phe Gly Asp Asp Lys Gly Leu Arg Asp Val Val Leu Asn Phe
305                 310                 315                 320

Val Ile Ala Gly Arg Asp Thr Thr Ala Thr Thr Leu Ser Trp Phe Thr
                325                 330                 335

Tyr Met Ala Met Thr His Pro Ala Val Ala Glu Lys Leu Arg Arg Glu
            340                 345                 350
```

```
Leu Ala Ala Phe Glu Ala Asp Arg Ala Arg Glu Gly Val Ala Leu
            355                 360                 365

Val Pro Cys Ser Asp Gly Glu Gly Ala Asp Glu Ala Phe Ala Ala Arg
370                 375                 380

Val Ala Gln Phe Ala Gly Leu Leu Ser Tyr Asp Gly Leu Gly Lys Leu
385                 390                 395                 400

Val Tyr Leu His Ala Cys Val Thr Glu Thr Leu Arg Leu Tyr Pro Ala
                405                 410                 415

Val Pro Gln Asp Pro Lys Gly Ile Ala Glu Asp Val Leu Pro Asp
            420                 425                 430

Gly Thr Lys Val Arg Ala Gly Gly Met Val Thr Tyr Val Pro Tyr Ser
            435                 440                 445

Met Gly Arg Met Glu Tyr Asn Trp Gly Pro Asp Ala Ala Ser Phe Arg
450                 455                 460

Pro Glu Arg Trp Ile Gly Asp Asp Gly Ala Phe Arg Asn Ala Ser Pro
465                 470                 475                 480

Phe Lys Phe Thr Ala Phe Gln Ala Gly Pro Arg Ile Cys Leu Gly Lys
                485                 490                 495

Asp Ser Ala Tyr Leu Gln Met Lys Met Ala Leu Ala Ile Leu Cys Arg
            500                 505                 510

Phe Phe Arg Phe Glu Leu Val Glu Gly His Pro Val Lys Tyr Arg Met
            515                 520                 525

Met Thr Ile Leu Ser Met Ala His Gly Leu Lys Val Arg Val Ser Arg
            530                 535                 540

Ala Pro Leu Ala
545

<210> SEQ ID NO 9
<211> LENGTH: 1929
<212> TYPE: DNA
<213> ORGANISM: Aegilops speltoides

<400> SEQUENCE: 9
atggaggaag ctcaccttgg catgccgtcg acgacggcct tcttcccgct ggcagggctc      60
cacaagttca tggccatctt cctcgtgttc ctctcgtgga tcctggtcca ctggtggagc     120
ctgaggaagc agaaggggcc gaggtcatgg ccggtcatcg cgccacgct ggagcagctg      180 aggaactact accggatgca cgactggctc gtggagtacc tgtccaagca ccggacggtc     240
accgtcgaca tgcccttcac ctcctacacc tacatcgccg acccggtgaa cgtcgagcat     300
gtgctcaaga ccaacttcaa caattacccc aaggtgaaac aatcctcgag atgtcagtca     360
aggttcggta taatcggtac tgacagtgtt acaaatgtct gaaatctgaa attgtgtgtg     420
tagggggagg tgtacaggtc ctacatggac gtgctgctcg gcgacggcat attcaacgcc     480
gacggcgagc tctggaggaa gcagaggaag acggcgagct tcgagttcgc ttccaagaac     540
ctgagagact tcagcacgat cgtgttccgg gagtactccc tgaagctgtc cagcatcctg     600
agccaggctt gcaaggccgg caaagttgtg gacatgcagg taactgaact cttcccttg      660 gtcatctgaa cgttgatttc ttggacaaaa tttcaagatt gtgacgcgag cgagccaatt     720
caggagctgt acatgaggat gacgctggac tcgatctgca aggtggggtt cggggtggag     780
atcggcacgc tgtcgccgga gctgccggag aacagcttcg cgcaggcctt cgacgccgcc     840
aacatcatcg tgacgctgcg gttcatcgac ccgctgtggc gcgtgaagaa gttcctgcac     900
gtcggctcgg aggcgctgct ggagcagagc atcaagctcg tcgacgagtt cacctacagc     960
```

```
gtcatccgcc ggcgcaaggc cgagatcgtg caggcccggg ccagcggcaa gcaggagaag    1020
gtgcgtacgc ggtcatcgtc attcgtcaag ctcccgatcg ctggtttgtg cagatgccat    1080
tgatcactga cacattaact gggcgcgcag atcaagcacg acatactgtc gcggttcatc    1140
gagctgggcg aggccggcgg cgacgacggc ggcagcctgt cggggacga caagggcctc    1200 cgcgacgtgg tgctcaactt cgtgatcgcc gggcgggaca ccacggccac gacgctctcc    1260
tggttcacct acatggccat gacgcacccg gacgtggccg agaagctccg ccgcgagctg    1320
gccgccttcg agtccgagcg cgcccgcgag gagggcgtcg ctctggtccc ctgcagcgac    1380
ggcgagggct ccgacgaggc cttcgccgcc cgcgtggcgc agttcgcggg gctcctgagc    1440
tacgacgggc tcgggaagct ggtgtacctc cacgcgtgcg tgacggagac gctgcgcctg    1500
tacccggcgt gccgcaggat cccaagggc atcgcggagg acgacgtgct cccggacggc    1560
accaaggtgc gcgccggcgg gatggtgacg tacgtgccct actccatggg gcggatggag    1620
tacaactggg gccccgacgc cgccagcttc cggccggagc ggtggatcgg cgacgatggc    1680
gccttccgca acgcgtcgcc gttcaagttc acggcgttcc aggcggggcc gcggatctgc    1740
ctgggcaagg actcggcgta cctgcagatg aagatggcgc tggccatcct gtgcaggttc    1800
ttcaggttcg agctcgtgga gggccacccc gtcaagtacc gcatgatgac catcctctcc    1860
atggcgcacg gcctcaaggt ccgcgtctcc agggcgccgc tcgcctgatc ttgatctggt    1920
tccggcgag                                                           1929

<210> SEQ ID NO 10
<211> LENGTH: 547
<212> TYPE: PRT
<213> ORGANISM: Aegilops speltoides

<400> SEQUENCE: 10

Met Glu Glu Ala His Leu Gly Met Pro Ser Thr Thr Ala Phe Phe Pro
1               5                   10                  15

Leu Ala Gly Leu His Lys Phe Met Ala Ile Phe Leu Val Phe Leu Ser
                20                  25                  30

Trp Ile Leu Val His Trp Ser Leu Arg Lys Gln Lys Gly Pro Arg
            35                  40                  45

Ser Trp Pro Val Ile Gly Ala Thr Leu Glu Gln Leu Arg Asn Tyr Tyr
    50                  55                  60

Arg Met His Asp Trp Leu Val Glu Tyr Leu Ser Lys His Arg Thr Val
65                  70                  75                  80

Thr Val Asp Met Pro Phe Thr Ser Tyr Thr Tyr Ile Ala Asp Pro Val
                85                  90                  95

Asn Val Glu His Val Leu Lys Thr Asn Phe Asn Asn Tyr Pro Lys Gly
                100                 105                 110

Glu Val Tyr Arg Ser Tyr Met Asp Val Leu Leu Gly Asp Gly Ile Phe
            115                 120                 125

Asn Ala Asp Gly Glu Leu Trp Arg Lys Gln Arg Lys Thr Ala Ser Phe
        130                 135                 140

Glu Phe Ala Ser Lys Asn Leu Arg Asp Phe Ser Thr Ile Val Phe Arg
145                 150                 155                 160

Glu Tyr Ser Leu Lys Leu Ser Ser Ile Leu Ser Gln Ala Cys Lys Ala
                165                 170                 175

Gly Lys Val Val Asp Met Gln Glu Leu Tyr Met Arg Thr Leu Asp
                180                 185                 190
```

```
Ser Ile Cys Lys Val Gly Phe Gly Val Glu Ile Gly Thr Leu Ser Pro
            195                 200                 205

Glu Leu Pro Glu Asn Ser Phe Ala Gln Ala Phe Asp Ala Ala Asn Ile
        210                 215                 220

Ile Val Thr Leu Arg Phe Ile Asp Pro Leu Trp Arg Val Lys Lys Phe
225                 230                 235                 240

Leu His Val Gly Ser Glu Ala Leu Leu Glu Gln Ser Ile Lys Leu Val
                245                 250                 255

Asp Glu Phe Thr Tyr Ser Val Ile Arg Arg Lys Ala Glu Ile Val
            260                 265                 270

Gln Ala Arg Ala Ser Gly Lys Gln Glu Lys Ile Lys His Asp Ile Leu
        275                 280                 285

Ser Arg Phe Ile Glu Leu Gly Glu Ala Gly Asp Gly Gly Ser
290                 295                 300

Leu Phe Gly Asp Asp Lys Gly Leu Arg Asp Val Val Leu Asn Phe Val
305                 310                 315                 320

Ile Ala Gly Arg Asp Thr Thr Ala Thr Thr Leu Ser Trp Phe Thr Tyr
                325                 330                 335

Met Ala Met Thr His Pro Asp Val Ala Glu Lys Leu Arg Arg Glu Leu
            340                 345                 350

Ala Ala Phe Glu Ser Glu Arg Ala Arg Glu Glu Gly Val Ala Leu Val
        355                 360                 365

Pro Cys Ser Asp Gly Glu Gly Ser Asp Glu Ala Phe Ala Ala Arg Val
370                 375                 380

Ala Gln Phe Ala Gly Leu Leu Ser Tyr Asp Gly Leu Gly Lys Leu Val
385                 390                 395                 400

Tyr Leu His Ala Cys Val Thr Glu Thr Leu Arg Leu Tyr Pro Ala Val
                405                 410                 415

Pro Gln Asp Pro Lys Gly Ile Ala Glu Asp Val Leu Pro Asp Gly
            420                 425                 430

Thr Lys Val Arg Ala Gly Gly Met Val Thr Tyr Val Pro Tyr Ser Met
        435                 440                 445

Gly Arg Met Glu Tyr Asn Trp Gly Pro Asp Ala Ala Ser Phe Arg Pro
450                 455                 460

Glu Arg Trp Ile Gly Asp Asp Gly Ala Phe Arg Asn Ala Ser Pro Phe
465                 470                 475                 480

Lys Phe Thr Ala Phe Gln Ala Gly Pro Arg Ile Cys Leu Gly Lys Asp
                485                 490                 495

Ser Ala Tyr Leu Gln Met Lys Met Ala Leu Ala Ile Leu Cys Arg Phe
            500                 505                 510

Phe Arg Phe Glu Leu Val Glu Gly His Pro Val Lys Tyr Arg Met Met
        515                 520                 525

Thr Ile Leu Ser Met Ala His Gly Leu Lys Val Arg Val Ser Arg Ala
530                 535                 540

Pro Leu Ala
545

<210> SEQ ID NO 11
<211> LENGTH: 1930
<212> TYPE: DNA
<213> ORGANISM: Aegilops tauschii

<400> SEQUENCE: 11
atggaggaag ctcacggcgg catgccgtcg acgacggcct tcttcccgct ggcagggctc      60
```

```
cacaagttca tggccatctt cctcgtgttc ctctcgtgga tcttggtcca ctggtggagc    120
ctgaggaagc agaaggggcc gaggtcatgg ccggtcatcg gcgcgacgct ggagcagctg    180
aggaactact accggatgca cgactggctc gtggagtacc tgtccaagca ccggacggtg    240
accgtcgaca tgcccttcac ctcctacacc tacatcgccg acccggtgaa cgtcgagcat    300
gtgctcaaga ccaacttcaa caattacccc aaggtgaaac aatcctcgag atgtcagtaa    360
aggttcagta taatcggtac tgacagtgtt acaaatgtct gaaatctgaa attgtatgtg    420 taggggagg tgtacaggtc ctacatggac gtgctgctcg gcgacggcat attcaacgcc     480
gacggcgagc tctggaggaa gcagaggaag acggcgagct tcgagttcgc ttccaagaac    540
ttgagagact tcagcacgat cgtgttcagg gagtactccc tgaagctgtc cagcatactg    600
agccaggctt gcaaggccgg caaagttgtg gacatgcagg taactgaact cattcccttg    660
gtcatctgaa cgttgatttc ttggacaaaa tttcaagatt ctgacgcgag cgagcgaatt    720
caggagctgt atatgaggat gacgctggac tcgatctgca aagtggggtt cggagtcgag    780
atcggcacgc tgtcgccgga gctgccggag aacagcttcg cgcaggcgtt cgacgccgcc    840
aacatcatcg tgacgctgcg gttcatcgac ccgctgtggc gcgtgaagaa gttcctgcac    900
gtcggctcgg aggcgctgct ggagcagagc atcaagctcg tcgacgagtt cacctacagc    960
gtcatccgcc ggcgcaaggc cgagatcgtg caggcccggg ccagcggcaa gcaggagaag   1020
gtgcgtgcgt ggtcatcgtc attcgtcaag ctcccggtcg ctggtttgtg tagatgccat   1080
ggatcactga cacactaact gggcgcgcag atcaagcacg acatactgtc gcggttcatc   1140
gagctgggcg aggccggcgg cgacgacggc ggcagtctgt tcggggacga caagggcctc   1200
cgcgacgtgg tgctcaactt cgtgatcgcc gggcgggaca ccacggccac gacgctgtcc   1260
tggttcacct acatggccat gacgcacccg gacgtggccg agaagctccg ccgcgagctg   1320
gccgccttcg aggcggagcg cgcccgcgag gatggcgtcg ctctggtccc ctgcggcgac   1380
ggcgagggct ccgacgaggc cttcgctgcc cgcgtggcgc agttcgcggg gttcctgagc   1440
tacgacggcc tcgggaagct ggtgtacctc cacgcgtgcg tgacggagac gctgcgcctg   1500
tacccggcgt gccgcagga ccccaagggc atcgcgagg acgacgtgct cccggacggc      1560
accaaggtgc gcgccggcgg gatggtgacg tacgtgccct actccatggg gcggatggag   1620
tacaactggg ccccgacgc cgccagcttc cggccggagc ggtggatcgg cgacgacggc     1680
gccttccgca acgcgtcgcc gttcaagttc acggcgttcc aggcggggcc gcggatttgc   1740
ctcggcaagg actcggcgta cctgcagatg aagatggcgc tggcaatcct gtgcaggttc   1800
ttcaggttcg agctcgtgga gggccacccc gtcaagtacc gcatgatgac catcctctcc   1860
atggcgcacg gcctcaaggt ccgcgtctcc agggcgccgc tcgcctgatc ttgatctggt   1920
tccggcgagg                                                         1930
```

<210> SEQ ID NO 12
<211> LENGTH: 547
<212> TYPE: PRT
<213> ORGANISM: Aegilops tauschii

<400> SEQUENCE: 12

```
Met Glu Glu Ala His Gly Gly Met Pro Ser Thr Thr Ala Phe Phe Pro
1               5                   10                  15

Leu Ala Gly Leu His Lys Phe Met Ala Ile Phe Leu Val Phe Leu Ser
            20                  25                  30

Trp Ile Leu Val His Trp Trp Ser Leu Arg Lys Gln Lys Gly Pro Arg
```

```
             35                  40                  45
Ser Trp Pro Val Ile Gly Ala Thr Leu Glu Gln Leu Arg Asn Tyr Tyr
 50                  55                  60

Arg Met His Asp Trp Leu Val Glu Tyr Leu Ser Lys His Arg Thr Val
 65                  70                  75                  80

Thr Val Asp Met Pro Phe Thr Ser Tyr Thr Tyr Ile Ala Asp Pro Val
                 85                  90                  95

Asn Val Glu His Val Leu Lys Thr Asn Phe Asn Asn Tyr Pro Lys Gly
             100                 105                 110

Glu Val Tyr Arg Ser Tyr Met Asp Val Leu Leu Gly Asp Gly Ile Phe
             115                 120                 125

Asn Ala Asp Gly Glu Leu Trp Arg Lys Gln Arg Lys Thr Ala Ser Phe
 130                 135                 140

Glu Phe Ala Ser Lys Asn Leu Arg Asp Phe Ser Thr Ile Val Phe Arg
145                 150                 155                 160

Glu Tyr Ser Leu Lys Leu Ser Ser Ile Leu Ser Gln Ala Cys Lys Ala
                 165                 170                 175

Gly Lys Val Val Asp Met Gln Glu Leu Tyr Met Arg Met Thr Leu Asp
             180                 185                 190

Ser Ile Cys Lys Val Gly Phe Gly Val Glu Ile Gly Thr Leu Ser Pro
             195                 200                 205

Glu Leu Pro Glu Asn Ser Phe Ala Gln Ala Phe Asp Ala Ala Asn Ile
210                 215                 220

Ile Val Thr Leu Arg Phe Ile Asp Pro Leu Trp Arg Val Lys Lys Phe
225                 230                 235                 240

Leu His Val Gly Ser Glu Ala Leu Leu Glu Gln Ser Ile Lys Leu Val
                 245                 250                 255

Asp Glu Phe Thr Tyr Ser Val Ile Arg Arg Lys Ala Glu Ile Val
             260                 265                 270

Gln Ala Arg Ala Ser Gly Lys Gln Glu Lys Ile Lys His Asp Ile Leu
             275                 280                 285

Ser Arg Phe Ile Glu Leu Gly Glu Ala Gly Asp Asp Gly Gly Ser
290                 295                 300

Leu Phe Gly Asp Asp Lys Gly Leu Arg Asp Val Val Leu Asn Phe Val
305                 310                 315                 320

Ile Ala Gly Arg Asp Thr Thr Ala Thr Thr Leu Ser Trp Phe Thr Tyr
                 325                 330                 335

Met Ala Met Thr His Pro Asp Val Ala Glu Lys Leu Arg Arg Glu Leu
             340                 345                 350

Ala Ala Phe Glu Ala Glu Arg Ala Arg Glu Asp Gly Val Ala Leu Val
             355                 360                 365

Pro Cys Gly Asp Gly Glu Gly Ser Asp Glu Ala Phe Ala Ala Arg Val
370                 375                 380

Ala Gln Phe Ala Gly Phe Leu Ser Tyr Asp Gly Leu Gly Lys Leu Val
385                 390                 395                 400

Tyr Leu His Ala Cys Val Thr Glu Thr Leu Arg Leu Tyr Pro Ala Val
                 405                 410                 415

Pro Gln Asp Pro Lys Gly Ile Ala Glu Asp Val Leu Pro Asp Gly
             420                 425                 430

Thr Lys Val Arg Ala Gly Gly Met Val Thr Tyr Val Pro Tyr Ser Met
             435                 440                 445

Gly Arg Met Glu Tyr Asn Trp Gly Pro Asp Ala Ala Ser Phe Arg Pro
450                 455                 460
```

Glu Arg Trp Ile Gly Asp Asp Gly Ala Phe Arg Asn Ala Ser Pro Phe
465                 470                 475                 480

Lys Phe Thr Ala Phe Gln Ala Gly Pro Arg Ile Cys Leu Gly Lys Asp
                485                 490                 495

Ser Ala Tyr Leu Gln Met Lys Met Ala Leu Ala Ile Leu Cys Arg Phe
            500                 505                 510

Phe Arg Phe Glu Leu Val Glu Gly His Pro Val Lys Tyr Arg Met Met
        515                 520                 525

Thr Ile Leu Ser Met Ala His Gly Leu Lys Val Arg Val Ser Arg Ala
    530                 535                 540

Pro Leu Ala
545

<210> SEQ ID NO 13
<211> LENGTH: 1581
<212> TYPE: DNA
<213> ORGANISM: Triticum urartu

<400> SEQUENCE: 13

```
atggaagaga agaagccgcg gcggcaggga gccgcaggac gcgatggcat cgtgcagtac      60
ccgcacctct tcatcgcggc cctggcgctg ccctggtcc tcatggaccc cttccacctc     120
ggcccgctgg ccgggatcga ctaccggccg gtgaagcacg agctggcgcc gtacagggag     180
gtcatgcagc gctggccgag ggacaacggc agccgcctca ggctcggcag gctcgagttc     240
gtcaacgagg tgttcgggcc ggagtccatc gagttcgacc gccagggccg cgggccctac     300
gccgggctcg ccgacggccg cgtcgtgcgg tggatggggg acaaggccgg gtgggagacg     360
ttcgccgtca tgaatcctga ctggtattgg cttactgcag aaaaaccata gcttacctgt     420
gtgtgtgcaa actaaaatag tttctttcgg aaaaaaaaag gtcggagaaa gtttgtgcta     480
acggagtgga gtcgacgacg aagaagcagc acgggaagga gaagtggtgc ggccggcctc     540
tcgggctgag gttccacagg gagaccggcg agctcttcat cgccgacgcg tactatgggc     600
tcatggccgt tggcgaaagc ggcggcgtgg cgacctccct ggcgagggag gccggcgggg     660
acccggtcca cttcgccaac gacctcgaca tccacatgaa cggctcgata ttcttcaccg     720
acacgagcac gagatacagc agaaagtgag cggagtactg ctgccgatct ccttttcctg     780
ttcttgagat ttgtgtttga caaatgactg atcatgcagg gaccatttga acattttgct     840
ggaaggagaa ggcacgggga ggctgctgag atatgaccga aaaccggtg ccgttcatgt     900
cgtgctcaac gggctggtct tcccaaacgg cgtgcagatc tcacaggacc agcaatttct     960
cctcttctcc gagacaacaa actgcaggtg agataaactc aggttttcag tatgatccgg    1020
ctcgagagat ccaggaactg atgacgcctt tattaatcgg ctcatgcatg cacactagga    1080
tcatgaggta ctggctggaa ggtccaagag cgggccaggt ggaggtgttc gcgaacctgc    1140
cggggttccc cgacaacgtg cgcttgaaca gcaaggggca gttctgggtg cgatcgact    1200
gctgccggac gccgacgcag gaggtgttcg cgcggtggcc gtggctgcgg accgcctact    1260
tcaagatccc ggtgtcgatg aagacgctgg ggaagatggt gagcatgaag atgtacacgc    1320
ttctcgcgct cctcgacggc gaggggaacg tggtcgaggt actcgaggac cggggcggcg    1380
aggtgatgaa gctggtgagc gaggtgaggg aggtggaccg gaggctgtgg atcgggaccg    1440
ttgcgcacaa ccacatcgcc acgatcccct acccgttgga ctagagtgtg tagtgtctca    1500
tttgatttgc tggttttata ttagcaagga ggtgtatcag tttatggttt gcttgtttat    1560
```
tgggttcgtg tgatgatcgt g                                                    1581

<210> SEQ ID NO 14
<211> LENGTH: 413
<212> TYPE: PRT
<213> ORGANISM: Triticum urartu

<400> SEQUENCE: 14

Met Glu Glu Lys Lys Pro Arg Arg Gln Gly Ala Ala Gly Arg Asp Gly
1               5                   10                  15

Ile Val Gln Tyr Pro His Leu Phe Ile Ala Ala Leu Ala Leu Ala Leu
                20                  25                  30

Val Leu Met Asp Pro Phe His Leu Gly Pro Leu Ala Gly Ile Asp Tyr
            35                  40                  45

Arg Pro Val Lys His Glu Leu Ala Pro Tyr Arg Glu Val Met Gln Arg
        50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                85                  90                  95

Arg Gly Pro Tyr Ala Gly Leu Ala Asp Gly Arg Val Val Arg Trp Met
            100                 105                 110

Gly Asp Lys Ala Gly Trp Glu Thr Phe Ala Val Met Asn Pro Asp Trp
        115                 120                 125

Ser Glu Lys Val Cys Ala Asn Gly Val Glu Ser Thr Thr Lys Lys Gln
130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Ser Gly Gly Val Ala Thr Ser Leu Ala Arg Glu Ala
            180                 185                 190

Gly Gly Asp Pro Val His Phe Ala Asn Asp Leu Asp Ile His Met Asn
        195                 200                 205

Gly Ser Ile Phe Phe Thr Asp Thr Ser Thr Arg Tyr Ser Arg Lys Asp
210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                245                 250                 255

Phe Pro Asn Gly Val Gln Ile Ser Gln Asp Gln Gln Phe Leu Leu Phe
            260                 265                 270

Ser Glu Thr Thr Asn Cys Arg Ile Met Arg Tyr Trp Leu Glu Gly Pro
        275                 280                 285

Arg Ala Gly Gln Val Glu Val Phe Ala Asn Leu Pro Gly Phe Pro Asp
290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335

Thr Ala Tyr Phe Lys Ile Pro Val Ser Met Lys Thr Leu Gly Lys Met
            340                 345                 350

Val Ser Met Lys Met Tyr Thr Leu Leu Ala Leu Leu Asp Gly Glu Gly
        355                 360                 365

```
Asn Val Val Glu Val Leu Glu Asp Arg Gly Gly Glu Val Met Lys Leu
        370                 375                 380

Val Ser Glu Val Arg Glu Val Asp Arg Arg Leu Trp Ile Gly Thr Val
385                 390                 395                 400

Ala His Asn His Ile Ala Thr Ile Pro Tyr Pro Leu Asp
                405                 410

<210> SEQ ID NO 15
<211> LENGTH: 1536
<212> TYPE: DNA
<213> ORGANISM: Aegilops speltoides

<400> SEQUENCE: 15
atggaagaga agaagccgcg gcggcaggga gccgcagtac gcgatggcat cgtgcagtac      60
ccgcacctct tcatcgcggc cctggcgctg gccctggtcg tcatggaccc cttccacctc     120
ggcccgctgg ccgggatcga ctaccggccg gtgaagcacg agctggcgcc gtacagggag     180
gtcatgcagc gctggccgag ggacaacggc agcggctga gactcggcag gctcgagttc      240
gtcaacgagg tgttcgggcc ggagtccatc gagttcgacc gccagggccg cgggccctac     300
gccggcctcg ccgacggccg cgtcgtgcgg tggatggggg agaaggccgg gtgggagacg     360
ttcgccgtca tgaatcctga ctggtattgg cttactgcag ataaatccat agcttacctg     420
tgtgtttgca aactaaaatg gtttcttgga aaaaaaagg tcggagaaag tttgtgctaa      480
cggagtggag tcaacgacga agaagcagca cgggaaggag aagtggtgcg gccggcctct     540
cgggctgagg ttccacaggg agaccggcga gctcttcatc gccgacgcgt actatgggct     600
catggccgtc ggcgaaagcg gcggcgtggc gacctccctg caagggagg ccggcgggga     660 cccggtccac ttcgccaacg accttgacat ccacatgaac ggctcgatat tcttcaccga     720
cacgagcacg agatacagca gaaagtgagc gaactgctgc cgctgttctc cattttttgt     780
aatgagatgt tgtgtttgag tgtctgacac catgactgat catgcaggga ccatttgaac     840
attttgctgg aaggagaagg cacggggagg ctgctgagat atgaccgaga accggtgcc     900 gttcatgtcg tgctcaacgg gctggtcttc ccaaacggcg tgcagattc acaggaccag     960 caattctctc tcttctccga gacaacaaac tgcaggtgag ataaactcag attttcagta    1020
tgatccggct cgagagatcc aggaactgat gacggctcat gcacgcacgc taggatcatg    1080
aggtactggc tggaaggtcc aagagcgggc caggtggagg tgttcgcgaa cctgccgggg    1140
ttccccgaca cgtgcgcct gaacagcaag gggcagttct gggtggcgat cgactgctgc    1200
cggacgccga cgcaggaggt gttcgcgcgg tggccgtggc tgcggaccgc ctacttcaag    1260
atcccggtgt cgatgaagac gctggggaag atggtgagca tgaagatgta cacgcttctc    1320
gcgctcctcg acggcgaggg gaacgtcgtg gaggtgctcg aggaccgggg cggcgaggtg    1380
atgaagctgg tgagcgaggt gagggaggtg gaccggaggc tgtggatcgg accgttgcg    1440 cacaaccaca tcgccacgat cccttacccg ctggactaga gggagtgtgt agtgtccatt    1500
tgctggttta tattagcaag gaggtgtatc agttta                             1536

<210> SEQ ID NO 16
<211> LENGTH: 413
<212> TYPE: PRT
<213> ORGANISM: Aegilops speltoides

<400> SEQUENCE: 16

Met Glu Glu Lys Lys Pro Arg Arg Gln Gly Ala Ala Val Arg Asp Gly
1               5                   10                  15
```

Ile Val Gln Tyr Pro His Leu Phe Ile Ala Ala Leu Ala Leu Ala Leu
                 20                  25                  30

Val Val Met Asp Pro Phe His Leu Gly Pro Leu Ala Gly Ile Asp Tyr
             35                  40                  45

Arg Pro Val Lys His Glu Leu Ala Pro Tyr Arg Glu Val Met Gln Arg
50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                 85                  90                  95

Arg Gly Pro Tyr Ala Gly Leu Ala Asp Gly Arg Val Val Arg Trp Met
             100                 105                 110

Gly Glu Lys Ala Gly Trp Glu Thr Phe Ala Val Met Asn Pro Asp Trp
         115                 120                 125

Ser Glu Lys Val Cys Ala Asn Gly Val Glu Ser Thr Thr Lys Lys Gln
130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                 165                 170                 175

Ala Val Gly Glu Ser Gly Gly Val Ala Thr Ser Leu Ala Arg Glu Ala
             180                 185                 190

Gly Gly Asp Pro Val His Phe Ala Asn Asp Leu Asp Ile His Met Asn
         195                 200                 205

Gly Ser Ile Phe Phe Thr Asp Thr Ser Thr Arg Tyr Ser Arg Lys Asp
210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                 245                 250                 255

Phe Pro Asn Gly Val Gln Ile Ser Gln Asp Gln Gln Phe Leu Leu Phe
             260                 265                 270

Ser Glu Thr Thr Asn Cys Arg Ile Met Arg Tyr Trp Leu Glu Gly Pro
         275                 280                 285

Arg Ala Gly Gln Val Glu Val Phe Ala Asn Leu Pro Gly Phe Pro Asp
290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                 325                 330                 335

Thr Ala Tyr Phe Lys Ile Pro Val Ser Met Lys Thr Leu Gly Lys Met
             340                 345                 350

Val Ser Met Lys Met Tyr Thr Leu Leu Ala Leu Leu Asp Gly Glu Gly
         355                 360                 365

Asn Val Val Glu Val Leu Glu Asp Arg Gly Gly Glu Val Met Lys Leu
370                 375                 380

Val Ser Glu Val Arg Glu Val Asp Arg Arg Leu Trp Ile Gly Thr Val
385                 390                 395                 400

Ala His Asn His Ile Ala Thr Ile Pro Tyr Pro Leu Asp
             405                 410

<210> SEQ ID NO 17
<211> LENGTH: 1573

<212> TYPE: DNA
<213> ORGANISM: Aegilops tauschii

<400> SEQUENCE: 17

```
atggaagaga agaaaccgcg gcggcaggga gccgcagtac gcgatggcat cgtgcagtac      60
ccgcacctct tcatcgcggc cctggcgctg gccctggtcc tcatggaccc gttccacctc     120
ggcccgctgg ccgggatcga ctaccgaccg gtgaagcacg agctggcgcc gtacagggag     180
gtcatgcagc gctggccgag ggacaacggc agccgcctca ggctcggcag gctcgagttc     240
gtcaacgagg tgttcgggcc ggagtccatc gagttcgacc gccagggccg cgggccttac     300
gccgggctcg ccgacggccg cgtcgtgcgg tggatggggg acaaggccgg gtgggagacg     360
ttcgccgtca tgaatcctga ctggtactgg cttactgcag aaaaacccat agcttacctg     420
tgtgtgtgca gactaaaata gtttctttca taaaaaaaaa ggtcggagaa agtttgtgct     480
aacggagtgg agtcgacgac gaagaagcag cacgggaagg agaagtggtg cggccggcct     540
ctcggcctga ggttccacag ggagaccggc gagctcttca tcgccgacgc gtactatggg     600
ctcatggccg tcggcgaaag gggcggcgtg gcgacctccc tggcgaggga ggccggcggg     660
gacccggtcc acttcgccaa cgaccttgac atccacatga acggctcgat attcttcacc     720
gacacgagca cgagatacag cagaaagtga gcggagtact gctgccgatc tccttttttct    780
gttcttgaga tttgtgtttg acaaatgact gatcatgcag ggaccatttg aacattttgc     840
tggaaggaga aggcacgggg aggctgctga gatatgaccg agaaaccggt gccgttcatg     900
tcgtgctcaa cgggctggtc ttcccaaacg gcgtgcagat atcacaggac cagcaatttc     960
tcctcttctc cgagacaaca aactgcaggt gagataaact caggttttca gtatgatccg    1020
gctcgagaga tccaggaact gatgacggct catgcatgca cactaggatc atgaggtact    1080
ggctggaagg tccaagagcg ggccaggtgg aggtgttcgc gaacctgccg gggttccccg    1140
acaatgtgcg cctgaacagc aaggggcagt tctgggtggc catcgactgc tgccgtacgc    1200
cgacgcagga ggtgttcgcg cggtggccgt ggctgcggac cgcctacttc aagatcccgg    1260
tgtcgatgaa gacgctgggg aagatggtga gcatgaagat gtacacgctt ctcgcgctcc    1320
tcgacggcga ggggaacgtc gtggaggtgc tcgaggaccg gggcggcgag gtgatgaagc    1380
tggtgagcga ggtgagggag gtggaccgga ggctgtggat cgggaccgtt gcgcacaacc    1440
acatcgccac gatcccttac ccgctggact agagggagtg tgtagtgtcc catttgattt    1500
gctggtttta tattagcaag gaggtgtatc agtttatggt ttgcttgttc attgggttcg    1560
tgtgatgatc gtg                                                       1573
```

<210> SEQ ID NO 18
<211> LENGTH: 415
<212> TYPE: PRT
<213> ORGANISM: Aegilops tauschii

<400> SEQUENCE: 18

```
Met Glu Glu Lys Lys Pro Arg Arg Gln Gly Ala Ala Val Arg Asp Gly
1               5                   10                  15

Ile Val Gln Tyr Pro His Leu Phe Ile Ala Ala Leu Ala Leu Ala Leu
            20                  25                  30

Val Leu Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60
```

```
Trp Pro Arg Asp Asn Gly Ser Arg Leu Arg Leu Gly Arg Leu Glu Phe
 65                  70                  75                  80

Val Asn Glu Val Phe Gly Pro Glu Ser Ile Glu Phe Asp Arg Gln Gly
                 85                  90                  95

Arg Gly Pro Tyr Ala Gly Leu Ala Asp Gly Arg Val Val Arg Trp Met
            100                 105                 110

Gly Asp Lys Ala Gly Trp Glu Thr Phe Ala Val Met Asn Pro Asp Trp
        115                 120                 125

Tyr Trp Ser Glu Lys Val Cys Ala Asn Gly Val Glu Ser Thr Thr Lys
    130                 135                 140

Lys Gln His Gly Lys Glu Lys Trp Cys Gly Arg Pro Leu Gly Leu Arg
145                 150                 155                 160

Phe His Arg Glu Thr Gly Glu Leu Phe Ile Ala Asp Ala Tyr Tyr Gly
                165                 170                 175

Leu Met Ala Val Gly Glu Arg Gly Val Ala Thr Ser Leu Ala Arg
            180                 185                 190

Glu Ala Gly Gly Asp Pro Val His Phe Ala Asn Asp Leu Asp Ile His
        195                 200                 205

Met Asn Gly Ser Ile Phe Phe Thr Asp Thr Ser Thr Arg Tyr Ser Arg
    210                 215                 220

Lys Asp His Leu Asn Ile Leu Leu Glu Gly Glu Gly Thr Gly Arg Leu
225                 230                 235                 240

Leu Arg Tyr Asp Arg Glu Thr Gly Ala Val His Val Val Leu Asn Gly
                245                 250                 255

Leu Val Phe Pro Asn Gly Val Gln Ile Ser Gln Asp Gln Phe Leu
            260                 265                 270

Leu Phe Ser Glu Thr Thr Asn Cys Arg Ile Met Arg Tyr Trp Leu Glu
        275                 280                 285

Gly Pro Arg Ala Gly Gln Val Glu Val Phe Ala Asn Leu Pro Gly Phe
    290                 295                 300

Pro Asp Asn Val Arg Leu Asn Ser Lys Gly Gln Phe Trp Val Ala Ile
305                 310                 315                 320

Asp Cys Cys Arg Thr Pro Thr Gln Glu Val Phe Ala Arg Trp Pro Trp
                325                 330                 335

Leu Arg Thr Ala Tyr Phe Lys Ile Pro Val Ser Met Lys Thr Leu Gly
            340                 345                 350

Lys Met Val Ser Met Lys Met Tyr Thr Leu Leu Ala Leu Leu Asp Gly
        355                 360                 365

Glu Gly Asn Val Val Glu Val Leu Glu Asp Arg Gly Gly Glu Val Met
    370                 375                 380

Lys Leu Val Ser Glu Val Arg Glu Val Asp Arg Arg Leu Trp Ile Gly
385                 390                 395                 400

Thr Val Ala His Asn His Ile Ala Thr Ile Pro Tyr Pro Leu Asp
                405                 410                 415

<210> SEQ ID NO 19
<211> LENGTH: 10
<212> TYPE: PRT
<213> ORGANISM: Artificial
<220> FEATURE:
<223> OTHER INFORMATION: heme-binding domain of MS26
<220> FEATURE:
<221> NAME/KEY: misc_feature
<223> OTHER INFORMATION: Xaa = any amino acid
<220> FEATURE:
<221> NAME/KEY: misc_feature
<222> LOCATION: (2)..(3)
```

```
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 19

Phe Xaa Xaa Gly Xaa Arg Xaa Cys Xaa Gly
1               5                   10

<210> SEQ ID NO 20
<211> LENGTH: 9
<212> TYPE: PRT
<213> ORGANISM: Artificial
<220> FEATURE:
<223> OTHER INFORMATION: dioxygen binding domain
<220> FEATURE:
<221> NAME/KEY: misc_feature
<222> LOCATION: (1)..(10)
<223> OTHER INFORMATION: Xaa = any amino acid

<400> SEQUENCE: 20

Ala Gly Gly Xaa Asp Glu Thr Thr Ser
1               5

<210> SEQ ID NO 21
<211> LENGTH: 22
<212> TYPE: DNA
<213> ORGANISM: Triticum aestivum

<400> SEQUENCE: 21
gatggtgacg tacgtgccct ac                                            22

<210> SEQ ID NO 22
<211> LENGTH: 58
<212> TYPE: DNA
<213> ORGANISM: Artificial
<220> FEATURE:
<223> OTHER INFORMATION: primary PCR forward primer

<400> SEQUENCE: 22
ctacactctt tccctacacg acgctcttcc gatctaaccc gcggaggacg acgtgctc     58

<210> SEQ ID NO 23
<211> LENGTH: 54
<212> TYPE: DNA
<213> ORGANISM: Artificial
<220> FEATURE:
<223> OTHER INFORMATION: primary PCR reverse primer

<400> SEQUENCE: 23
caagcagaag acggcatacg agctcttccg atctcgtcgg ggccccagtt gtac         54

<210> SEQ ID NO 24
<211> LENGTH: 43
<212> TYPE: DNA
<213> ORGANISM: Artificial
<220> FEATURE:
<223> OTHER INFORMATION: secondary PCR forward primer

<400> SEQUENCE: 24
```

```
aatgatacgg cgaccaccga gatctacact ctttccctac acg          43
```

<210> SEQ ID NO 25
<211> LENGTH: 18
<212> TYPE: DNA
<213> ORGANISM: Artificial
<220> FEATURE:
<223> OTHER INFORMATION: secondary PCR reverse primer

<400> SEQUENCE: 25

```
caagcagaag acggcata                                       18
```

<210> SEQ ID NO 26
<211> LENGTH: 23
<212> TYPE: DNA
<213> ORGANISM: Artificial
<220> FEATURE:
<223> OTHER INFORMATION: UNIMS26 5'-2 primer

<400> SEQUENCE: 26

```
gacgtggtgc tcaacttcgt gat                                 23
```

<210> SEQ ID NO 27
<211> LENGTH: 23
<212> TYPE: DNA
<213> ORGANISM: Artificial
<220> FEATURE:
<223> OTHER INFORMATION: UNIMS26 3'-1 primer

<400> SEQUENCE: 27

```
gccatggaga ggatggtcat cat                                 23
```

<210> SEQ ID NO 28
<211> LENGTH: 112
<212> TYPE: DNA
<213> ORGANISM: Triticum urartu

<400> SEQUENCE: 28

```
ggaggacgac gtgctcccgg acggcaccaa ggtgcgcgcc ggcgggatgg tgacgtacgt   60
gccctactcc atgggcgga tggagtataa ctggggcccc gacgccgcca gc           112
```

<210> SEQ ID NO 29
<211> LENGTH: 112
<212> TYPE: DNA
<213> ORGANISM: Aegilops speltoides

<400> SEQUENCE: 29

```
ggaggacgac gtgctcccgg acggcaccaa ggtgcgcgcc ggcgggatgg tgacgtacgt   60
gccctactcc atgggcgga tggagtacaa ctggggcccc gacgccgcca gc           112
```

<210> SEQ ID NO 30
<211> LENGTH: 112
<212> TYPE: DNA
<213> ORGANISM: Aegilops tauschii

<400> SEQUENCE: 30

```
ggaggacgac gtgctcccgg acggcaccaa ggtgcgcgcc ggcgggatgg tgacgtacgt   60
gccctactcc atgggcgga tggagtacaa ctggggcccc gacgccgcca gc           112
```

<210> SEQ ID NO 31
<211> LENGTH: 112
<212> TYPE: DNA

<213> ORGANISM: Zea mays

<400> SEQUENCE: 31

```
ggaggacgac gtgctgccgg acgggacgaa ggtgagggcc ggcgggatgg tgacgtacgt      60
gccctactcg atggggcgga tggagtacaa ctggggcccc gacgcggcga gc             112
```

<210> SEQ ID NO 32
<211> LENGTH: 112
<212> TYPE: DNA
<213> ORGANISM: Sorghum bicolor

<400> SEQUENCE: 32

```
ggaggacgac gtgctgccgg acgggacgaa ggtgagggcc ggcgggatgg tgacgtacgt      60
gccctactcg atggggcgga tggagtacaa ctggggaccc gacgcggcga gc             112
```

<210> SEQ ID NO 33
<211> LENGTH: 112
<212> TYPE: DNA
<213> ORGANISM: Oryza sativa

<400> SEQUENCE: 33

```
ggaggacgac gtgctccccg acggcaccaa ggtgcgcgcc ggcgggatgg tgacgtacgt      60
gccctactcc atggggagga tggagtacaa ctggggcccc gacgcggcga gc             112
```

<210> SEQ ID NO 34
<211> LENGTH: 100
<212> TYPE: DNA
<213> ORGANISM: Triticum aestivum

<400> SEQUENCE: 34

```
cgcggaggac gacgtgctcc cggacggcac caaggtgcgc gccggcggga tggtgacgta      60
cgtgccctac tccatggggc ggatggagta caactggggc                           100
```

<210> SEQ ID NO 35
<211> LENGTH: 77
<212> TYPE: DNA
<213> ORGANISM: Triticum aestivum

<400> SEQUENCE: 35

```
aacccgcgga ggacgacgtg ctcccggacg gcaccaaggt gccctactcc atggggcgga      60
tggagtacaa ctggggc                                                     77
```

<210> SEQ ID NO 36
<211> LENGTH: 95
<212> TYPE: DNA
<213> ORGANISM: Triticum aestivum

<400> SEQUENCE: 36

```
aacccgcgga ggacgacgtg ctcccggacg gcaccaaggt gcgcgccggc gggatggtga      60
cgtactccat ggggcggatg gagtacaact ggggc                                 95
```

<210> SEQ ID NO 37
<211> LENGTH: 71
<212> TYPE: DNA
<213> ORGANISM: Triticum aestivum

<400> SEQUENCE: 37

```
aacccgcgga ggacgacgtg ctcccggacg gcaccaaggt gcgcgccggc gggatggagt      60
acaactgggg c                                                           71
```

<210> SEQ ID NO 38
<211> LENGTH: 100
<212> TYPE: DNA
<213> ORGANISM: Triticum aestivum

<400> SEQUENCE: 38
aacccgcgga ggacgacgtg ctcccggacg gcaccaaggt gcgcgccggc gggatggtga    60
cgtgccctac tccatggggc ggatggagta caactggggc                         100

<210> SEQ ID NO 39
<211> LENGTH: 77
<212> TYPE: DNA
<213> ORGANISM: Triticum aestivum

<400> SEQUENCE: 39
aacccgcgga ggacgacgtg ctcccggacg gcaccaacgt gccctactcc atggggcgga    60
tggagtacaa ctggggc                                                  77

<210> SEQ ID NO 40
<211> LENGTH: 94
<212> TYPE: DNA
<213> ORGANISM: Triticum aestivum

<400> SEQUENCE: 40
aacccgcgga ggacgacgtg ctcccggacg gcaccaaggt gcgcgccggc gggatggtga    60
cgtacccatg ggcggatgg agtacaactg gggc                                94

<210> SEQ ID NO 41
<211> LENGTH: 87
<212> TYPE: DNA
<213> ORGANISM: Triticum aestivum

<400> SEQUENCE: 41
aacccgcgga ggacgacgtg ctcccggacg gcaccaaggt gcgcgccggc gggatactcc    60
atggggcgga tggagtacaa ctggggc                                       87

<210> SEQ ID NO 42
<211> LENGTH: 81
<212> TYPE: DNA
<213> ORGANISM: Triticum aestivum

<400> SEQUENCE: 42
aacccgcgga ggacgacgtg ctcccggacg gcaccaaggt acgtgcccta ctccatgggg    60
cggatggagt acaactgggg c                                             81

<210> SEQ ID NO 43
<211> LENGTH: 98
<212> TYPE: DNA
<213> ORGANISM: Triticum aestivum

<400> SEQUENCE: 43
aacccgcgga ggacgacgtg ctcccggacg gcaccaaggt gcgcgccggc gggatggtga    60
cgtactactc catgggcgg atggagtaca actggggc                            98

<210> SEQ ID NO 44
<211> LENGTH: 76
<212> TYPE: DNA
<213> ORGANISM: Triticum aestivum

<400> SEQUENCE: 44
aacccgcgga ggacgacgtg ctcccggacg gcaccaaggt gcgcgccggc gggatgtcca    60
tggggcggat ggagta    76

<210> SEQ ID NO 45
<211> LENGTH: 156
<212> TYPE: DNA
<213> ORGANISM: Triticum aestivum

<400> SEQUENCE: 45
ctgcgcctgt accggcggt gccgcaggac cccaagggca tcgcggagga cgacgtgctc    60
ccggacggca ccaaggtgcg cgccggcggg atggtgacgt acgtgcccta ctccatgggg   120
cggatggagt acaactgggg ccccgacgcc gccagc    156

<210> SEQ ID NO 46
<211> LENGTH: 66
<212> TYPE: DNA
<213> ORGANISM: Triticum aestivum

<400> SEQUENCE: 46
ctgcgcctgt acgtgcccta ctccatgggg cggatggagt acaactgggg ccccgacgcc    60
gccagc    66

<210> SEQ ID NO 47
<211> LENGTH: 60
<212> TYPE: DNA
<213> ORGANISM: Triticum aestivum

<400> SEQUENCE: 47
ctgcgcctgt accggcggt gccgcaggac cccaagggca tcgcggagga cgacgtcggc    60

<210> SEQ ID NO 48
<211> LENGTH: 133
<212> TYPE: DNA
<213> ORGANISM: Triticum aestivum

<400> SEQUENCE: 48
ctccgcctgt accggcggt gccgcaggac cccaagggca tcgcggagga cgacgtgctc    60
ccggacggca ccaaggtacg tgccctactc catggggcgg atggagtaca actggggccc   120
cgacgccgcc agc    133

<210> SEQ ID NO 49
<211> LENGTH: 152
<212> TYPE: DNA
<213> ORGANISM: Triticum aestivum

<400> SEQUENCE: 49
ctgcgcctgt accggcggt gccgcaggac cccaagggca tcgcggagga cgacgtgctc    60
ccggacggca ccaaggtgcg cgccggcggg atggtgacgt gccctactcc atgggcgga   120 tggagtacaa ctggggcccc gacgccgcca gc    152

<210> SEQ ID NO 50
<211> LENGTH: 157
<212> TYPE: DNA
<213> ORGANISM: Triticum aestivum

<400> SEQUENCE: 50
ctccgcctgt accggcggt gccgcaggac cccaagggca tcgcggagga cgacgtgctc    60

```
ccggacggca ccaaggtgcg cgccggcggg atggtgacgt accgtgccct actccatggg      120
gcggatggag tacaactggg gccccgacgc cgccagc                               157

<210> SEQ ID NO 51
<211> LENGTH: 75
<212> TYPE: DNA
<213> ORGANISM: Triticum aestivum

<400> SEQUENCE: 51
ctccgcctgt acccggcggt gccgcaggac cccaagggca tcgcggagga cgacgtgctc      60
ccggacggca ccaag                                                       75

<210> SEQ ID NO 52
<211> LENGTH: 147
<212> TYPE: DNA
<213> ORGANISM: Triticum aestivum

<400> SEQUENCE: 52
ctccgcctgt acccggcggt gccgcaggac cccaagggca tcgcggagga cgacgtgctc      60
ccggacggca ccaaggtgcg cgccggcggg atggtgacgt actccatggg gcggatggag      120
tacaactggg gccccgacgc cgccagc                                          147
```